US012685790B2

(12) United States Patent
Barbato et al.

(10) Patent No.: US 12,685,790 B2
(45) Date of Patent: Jul. 21, 2026

(54) STABLE, CONCENTRATED RADIOPHARMACEUTICAL COMPOSITION

(71) Applicant: NOVARTIS AG, Basel (CH)

(72) Inventors: Donato Barbato, Ivrea (IT); Lorenza Fugazza, Ivrea (IT); Maurizio F. Mariani, Ivrea (IT); Francesca Orlandi, Ivrea (IT); Lorenzo Sacchetti, Turin (IT); Mattia Tedesco, Alba (IT)

(73) Assignee: Novartis AG, Basel (CH)

( * ) Notice: Subject to any disclaimer, the term of this patent is extended or adjusted under 35 U.S.C. 154(b) by 158 days.

(21) Appl. No.: 17/753,762

(22) PCT Filed: Sep. 15, 2020

(86) PCT No.: PCT/EP2020/075767
§ 371 (c)(1),
(2) Date: Mar. 14, 2022

(87) PCT Pub. No.: WO2021/052960
PCT Pub. Date: Mar. 25, 2021

(65) Prior Publication Data

US 2022/0401593 A1 Dec. 22, 2022

(30) Foreign Application Priority Data

Sep. 16, 2019 (EP) .................................... 19197607

(51) Int. Cl.
*A61K 51/08* (2006.01)
*A61K 47/12* (2006.01)

(52) U.S. Cl.
CPC ............ *A61K 51/088* (2013.01); *A61K 47/12* (2013.01)

(58) Field of Classification Search
None
See application file for complete search history.

(56) References Cited

U.S. PATENT DOCUMENTS

| | | | | |
|---|---|---|---|---|
| 6,174,513 B1 | 1/2001 | Miller et al. | | |
| 2011/0206606 A1* | 8/2011 | Chen | A61P 35/00 | 424/1.65 |
| 2015/0217006 A1 | 8/2015 | Mcbride et al. | | |
| 2015/0265732 A1* | 9/2015 | Maina-Nock | A61K 51/08 | 424/1.69 |

FOREIGN PATENT DOCUMENTS

| | | |
|---|---|---|
| WO | 2005009393 A2 | 2/2005 |
| WO | 2008009444 A1 | 1/2008 |
| WO | 2019032624 A1 | 2/2019 |

OTHER PUBLICATIONS

Ali (Kolliphor@ HS 15—An Enabler for Parenteral and Oral Formulations. American Pharmaceutical Review. Feb. 15, 2019.) (Year: 2019).*

Steffel (Rapid and Simple Methods for Labeling White Blood Cells and Platelets with Indium-111-0xine. Radiopharmcuiticals. 1987. (Year: 1987).*

Ghosh, et al., Stability Evaluation and Stabilization of a Gastrin-Releasing Peptide Receptor (GRPR) Targeting Imaging Pharmaceutical, Molecules, 24, 2878, Aug. 8, 2019.

Khoruzhaya, et al., Biopharmacy—a scientific direction in the development and improvement of medicines: Tutorial, 7-9, 2006.

Lau, et al., Positron Emission Tomography Imaging of the Gastrin-Releasing Peptide Receptor with a Novel Bombesin Analogue, ACS Omega, 4(1), 1470-1478, 2019.

Lemarpax, The Lifecycle of Radiopharmaceuticals: From Research to Clinical Use, 2026.

Iori, et al., Labelling of 90Y- and 177Lu-DOTA-Bioconjugates for Targeted Radionuclide Therapy: A Comparison among Manual, Semiautomated, and Fully Automated Synthesis, Contrast Media & Molecular Imaging, 2017, article ID 8160134, 2017.

Mukherjee, et al., Single vial kit formulation of DOTATATE for preparation of 177lu-labeled therapeutic radiopharmaceutical at hospital radiopharmacy, Journal of Labelled Compounds and Radiopharmaceuticals, 2015.

Perez-Malo, et al., Improved Efficacy of Synthesizing *M111-Labeled DOTA Complexes in Binary Mixtures of Water and Organic Solvents. A Combined Radio-and Physicochemical Study, Inorganic Chemistry, May 21, 2018, 6107-6117, 57(10).

* cited by examiner

*Primary Examiner* — Michael G. Hartley
*Assistant Examiner* — Samantha L Mejias
(74) *Attorney, Agent, or Firm* — Derek Denhart

(57) ABSTRACT

The present disclosure relates to radionuclide complex solutions of high concentration and of high chemical stability, that allows their use as drug product for diagnostic and/or therapeutic purposes. The stability of the drug product is achieved by at least one stabilizer against radiolytic degradation. The use of two stabilizers introduced during the manufacturing process at different stages was found to be of particular advantage.

8 Claims, No Drawings

STABLE, CONCENTRATED RADIOPHARMACEUTICAL COMPOSITION

FIELD OF THE INVENTION

The present disclosure relates to pharmaceutical composition with radiolabeled GRPR antagonist compound of high concentration and of high chemical and radiochemical stability that allows their use as commercial drug product for diagnostic and/or therapeutic purposes.

BACKGROUND OF THE INVENTION

Bombesin was first isolated from the European frog *Bombina bombina* and was demonstrated to mimic the mammalian gastrin-releasing peptide (GRP) and neuromedin B (NMB) [Scopinaro F, et al. Eur J Nucl Med Mol Imaging 2003, 30 (10): 1378-1382].

Gastrin-releasing peptide (GRP), a bombesin-like peptide growth factor, regulates numerous functions of the gastrointestinal and central nervous systems, including release of gastrointestinal hormones, smooth muscle cell contraction, and epithelial cell proliferation. It is a potent mitogen for physiologic and neoplastic tissues, and it may be involved in growth dysregulation and carcinogenesis.

The effects of GRP are primarily mediated through binding to its receptor, the GRP receptor (GRPR), a G protein-coupled receptor originally isolated from a small cell lung cancer cell line. Upregulation of the pathway of GRP/GRPR has been reported in several cancers, including breast, prostate, uterus, ovaries, colon, pancreas, stomach, lung (small and non-small cell), head and neck squamous cell cancer and in various cerebral and neural tumours.

In breast cancer, GRPR overexpression can reach very high density according to tumour type (e.g. 70-90% expression in ductal breast cancer specimens) [Van de Wiele C, et al. J Nucl Med 2001, 42 (11): 1722-1727].

GRPR are highly overexpressed in prostate cancer where studies in human prostate cancer cell-lines and xenograft models showed both high affinity (nM level) and high tumour uptake (% ID/g) but the relative expression of GRPR across evolving disease setting from early to: late stage has not been fully elucidated yet [Waters, et al. 2003, Br J Cancer. June 2; 88 (11): 1808-1816].

In colorectal patients, presence of GRP and expression of GRPR have been determined by immunohistochemistry in randomly selected colon cancers samples, including LN and metastatic lesions. Over 80% of samples aberrantly expressed either GRP or GRPR, and over 60% expressing both GRP and GRPR, whereas expression was not observed in adjacent normal healthy epithelium [Scopinaro F, et al. Cancer Biother Radiopharm 2002, 17 (3): 327-335].

GRP is physiologically present in pulmonary neuroendocrine cells and plays a role in stimulating lung development and maturation. However, it seems to also be involved in growth dysregulation and carcinogenesis. Stimulation of GRP leads to increasing the release of epidermal growth factor receptor (EGFR) ligands with subsequent activation of EGFR and mitogen-activated protein kinase downstream pathways. Using non-small cell lung cancer (NSCLC) cell lines it has been confirmed that EGF and GRP both stimulate NSCLC proliferation, and inhibition of either EGFR or GRPR resulted in cell death [Shariati F, et al. Nucl Med Commun 2014, 35 (6): 620-625].

In nuclear medicine, peptide receptor agonists have long been the ligands of choice for tracer development and utilization. The rationale behind the use of agonist-based constructs laid on to receptor-radioligand complex internalization enabling the high accumulation of radioactivity inside the target cells. In case of radionuclide-labelled peptides, the efficient receptor-mediated endocytosis in response to agonist stimulation provides high in vivo radioactivity uptake in targeted tissues, a crucial prerequisite for optimal imaging of malignancies. However, a paradigm shift occurred when receptor-selective peptide antagonists showed preferable biodistribution, including considerably greater in vivo tumour uptake, compared with highly potent agonists. A further advantage displayed by GRPR antagonists is a safer clinical use, not so much at tracer doses for the current diagnostic point of view, but in view of greater doses for potential therapeutic purposes, as the use of antagonists does not foresee acute biological adverse effects [Stoykow C, et al. Theranostics 2016, 6 (10): 1641-1650].

It was recently found that some GRPR-antagonists, like NeoB, can be radiolabeled with different radionuclides and could potentially be used for imaging and for treating GRPR-expressing cancers, for example but not limited to, prostate cancer and breast cancer.

In non-clinical models, [$^{68}$Ga]-NeoB and [$^{177}$Lu]-NeoB have shown high affinity to the GRPR expressed in breast, prostate, and Gastro Intestinal Stromal Tumor (GIST), as well as a low degree of internalization upon binding to the specific receptor. The ability of the radiolabeled peptide to target the GRPR expressing tumor has been confirmed in in vivo imaging and biodistribution studies in animal models [Dalm et al Journal of nuclear medicine 2017, Vol. 58(2): 293-299].

For this radiomedicinal application the target cell receptor binding moiety is typically linked to a chelating agent which is able to form a strong complex with the metal ions of a radionuclide. This radiopharmaceutical drug is then delivered to the target cell and the decay of the radionuclide is then releasing high energy electrons, positrons or alpha particles as well as gamma rays at the target site.

One technical problem with those radiopharmaceutical drug products is that the decay of the radionuclide occurs constantly, e.g. also during the manufacturing and during storage of the drug product, and the released high energy emissions induce the cleavage of the chemical bonds of the molecules which form part of the drug product. This is often referred to as radiolysis or radiolytic degradation. The radiolytic degradation of the receptor binding moiety of the drug may lead to a decrease in its efficacy to act as a diagnostic and/or therapeutic.

The poor stability of those radiopharmaceutical drug products and their lack of any significant shelf-life required that those drugs have so far to be manufactured as an individual patient's dose unit in the laboratories at the hospital and administered immediately to the patient who had to be present at that hospital already awaiting the radiological treatment.

To reduce radiolysis of radiopharmaceutical drug products and thus improve stability, various strategies have been explored with more or less success: The drug product may be stored at low temperatures, or produced in high dilution, or stabilizers may be added.

Adding stabilizers however may be problematic as those chemicals may have a negative impact on the complexation of the radionuclide into the chelating agent or may have a limited solubility and precipitate from the solution. Ethanol has been reported as stabilizer against radiolysis (WO 2008/009444). While ethanol might not have a negative impact on the complexation or a solubility issue, higher amounts of ethanol in an infusion solution may be physiologically problematic and may have a negative impact on the tolerability of the drug product.

Producing the drug product in high dilution has the disadvantage that large volumes of infusion solutions need to be administered to patients. For the convenience of patients and for drug tolerability reasons it would be highly desirable to provide the radiopharmaceutical drug product in a high concentration. Those highly concentrated solutions however are in particular prone to radiolysis. Therefore, there are contradictory positions between, on the one hand, avoiding radiolysis by dilution of the drug product but, on the other hand, avoiding patient discomfort during treatment by providing a concentrated drug solution. In Mathur et al. *Cancer Biotherapy and Radiopharmaceuticals,* 2017, 32 (7), 266-273 a product of high concentration has been reported and claimed being ready-to-use. However, that composition may be problematic with respect to tolerability as it contains high amounts of ethanol.

It remains therefore a challenge to design a ready-to-use radiopharmaceutical composition which can be produced at commercial scale and delivered as a sufficiently stable and sterile solution in a high concentration which leads to a for patient convenient small infusion volume and which has a composition of high physiological tolerability (e.g. a composition which does not contain ethanol).

SUMMARY OF THE INVENTION

The present inventors have now found a way to design and produce a highly concentrated radionuclide complex solution which is chemically and radiochemically very stable, even if stored at ambient or short term elevated temperatures so that it can be produced on commercial scale and supplied as ready-to-use radiopharmaceutical product.

The present disclosure is provided in various aspects as outlined in the following:

1. A pharmaceutical composition comprising:
   (a) a complex formed by
      (ai) a radionuclide, and
      (aii) a GRP receptor peptide antagonist binding moiety linked to a chelating agent; and;
   (b) at least two stabilizer against radiolytic degradation; and
   (c) optionally a surfactant.
2. The pharmaceutical composition according to embodiment 1, wherein said radionuclide is selected from $^{111}$In, $^{18}$F, $^{211}$At, $^{82}$Rb, $^{123}$I, $^{131}$I, $^{133}$mIn, $^{99}$mTc, $^{94}$mTc, $^{67}$Ga, $^{66}$Ga, $^{68}$Ga, $^{52}$Fe, $^{169}$Er, $^{72}$As, $^{97}$Ru, $^{203}$Pb, $^{212}$Pb, $^{62}$Cu, $^{64}$Cu, $^{67}$Cu, $^{186}$Re, $^{188}$Re, $^{86}$Y, $^{90}$Y, $^{51}$Cr, $^{52}$mMn, $^{157}$Gd, $^{177}$Lu, $^{161}$Tb, $^{69}$Yb, $^{175}$Yb, $^{105}$Rh, $^{166}$Dy, $^{166}$Ho, $^{153}$Sm, $^{149}$Pm, $^{151}$Pm, $^{172}$Tm, $^{121}$Sn, $^{117}$mSn, $^{213}$Bi, $^{212}$Bi, $^{142}$Pr, $^{143}$Pr, $^{198}$Au, $^{199}$Au, $^{89}$Zr, $^{225}$Ac, $^{43}$Sc, $^{44}$Sc and $^{47}$Sc, preferably selected from $^{111}$In, $^{177}$Lu, $^{225}$Ac and $^{68}$Ga, more preferably is $^{177}$Lu.
3. The pharmaceutical composition according to embodiment 1, wherein said radionuclide is present at a concentration that it provides a volumetric radioactivity of at least 370 MBq/mL (at EOP)±37 MBq/mL (±10%).
4. The pharmaceutical composition according to embodiment 1, wherein said chelating agent is selected from DOTA, DTPA, NTA, EDTA, DO3A, NOC and NOTA, preferably is DOTA.
5. The pharmaceutical composition according to embodiment 1, wherein said GRP receptor peptide antagonist binding moiety linked to a chelating agent is NeoB of formula (I):

(I)

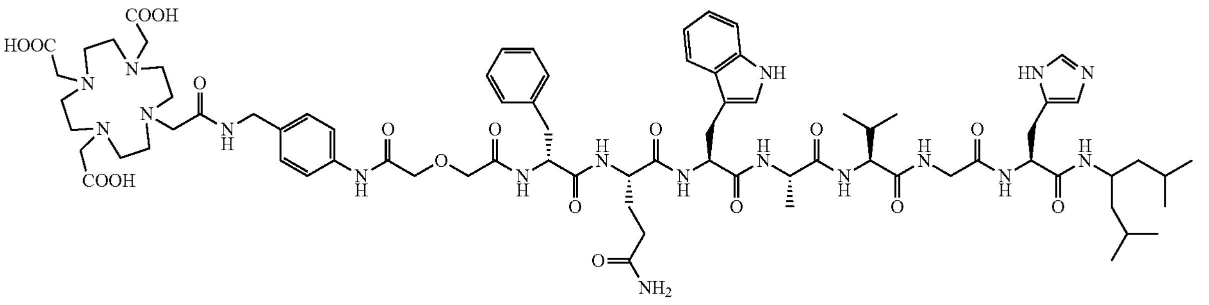

6. The pharmaceutical composition according to embodiment 1, wherein said at least two stabilizer are selected from gentisic acid (2,5-dihydroxybenzoic acid) or salts thereof, ascorbic acid (L-ascorbic acid, vitamin C) or salts thereof (e.g. sodium ascorbate), methionine, histidine, melatonine, ethanol, and Se-methionine, preferably selected from gentisic acid or salts thereof and ascorbic acid or salts thereof.
7. The pharmaceutical composition according to embodiment 6, wherein said at least two stabilizer are gentisic acid or salts thereof and ascorbic acid or salts thereof.
8. The pharmaceutical composition according to embodiment 7, wherein the ratio between gentisic acid and ascorbic acid is between 1:16 and 1:10, typically between 1:15 and 1:10, for example between 1:12 and 1:11.
9. The pharmaceutical composition according to embodiment 7 or 8, wherein said gentisic acid or salts thereof is present in a concentration of least 1000 µg/mL, for example between 1000 µg/ml and 1500 µg/mL.
10. The pharmaceutical composition according to embodiment 7 to 9, wherein said ascorbic acid or salts thereof is present in a concentration of at least 10000 µg/mL, preferably at least 12000 µg/mL, preferably at least 15000 µg/mL, for example between 12 000 and 18 000 µg/mL.
11. The pharmaceutical composition according to embodiment 7 to 10, wherein said gentisic acid or salts thereof is present in a concentration of least 1000 µg/mL, for example between 1000 µg/mL and 1500 µg/mL, and ascorbic acid or salts thereof is present in a concentration of 15000 µg/mL, for example between 12 000 and 18 000 µg/mL.
12. The pharmaceutical composition according to embodiment 1 to 11, wherein said pharmaceutical formulation has a radiochemical purity higher than 95% up to 72 hours, preferably higher than 98% up to 72 h.
13. The pharmaceutical composition according to embodiment 1 to 12, wherein said surfactant is a non-ionic surfactant.

14. The pharmaceutical composition according to embodiment 13, wherein said non-ionic surfactant is selected from Macrogol 15 Hydroxystearate, Poloxamer, Polysorbate 20, Polysorbate 80 or Polyvinylpyrrolidone average mol wt 10.000.
15. The pharmaceutical composition according to embodiment 14, wherein said non-ionic surfactant is Macrogol 15 Hydroxystearate.
16. The pharmaceutical composition according to embodiment 1-15, wherein said surfactant is present in a concentration of at least 5 μg/mL, preferably at least 25 μg/mL, and more preferably at least 50 μg/mL.
17. The pharmaceutical composition according to embodiment 16, wherein said surfactant is present in a concentration comprised between 5 g/mL and 5000 μg/mL, preferably between 25 μg/mL and 2000 μg/mL, and more preferably between 50 μg/mL and 1000 g/mL.
18. The pharmaceutical composition according to embodiment 17, wherein said surfactant is present in a concentration of 100 μg/mL.
19. A pharmaceutical composition comprising:
   - (a) a complex formed by
     - (ai) the radionuclide $^{177}$Lutetium (Lu-177), and
     - (aii) NeoB of formula (I):

(I)

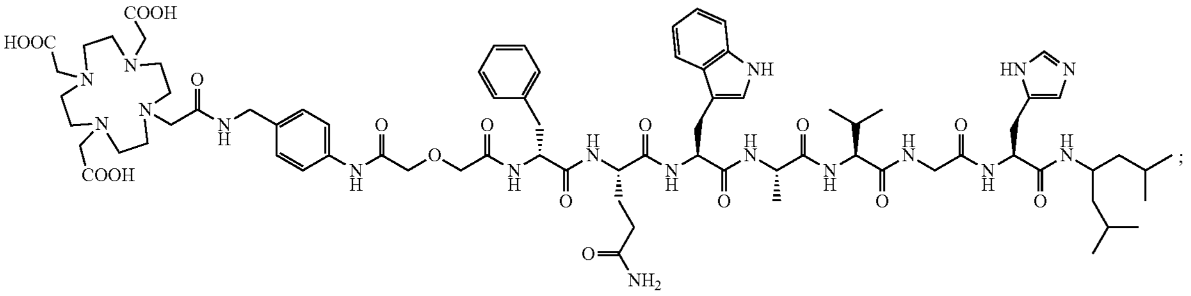

and;
   - (b) gentisic acid or salts thereof and ascorbic acid or salts thereof;
   - (c) optionally, Macrogol 15 Hydroxystearate,
   - (d) optionally, at least one other pharmaceutically acceptable excipient.

20. The pharmaceutical composition according to embodiment 19, wherein the at least one other pharmaceutically acceptable excipient is selected from buffer and/or solvent, and/or pH adjuster.
21. The pharmaceutical composition according to embodiment 20, wherein the buffer is selected from acetate buffer, citrate buffer and phosphate buffer, preferably acetate buffer.
22. The pharmaceutical composition according to embodiment 20 or 21, wherein the solvent is water for injection.
23. The pharmaceutical composition according to embodiment 20, 21 or 22, wherein the pH adjuster is NaOH.
24. A pharmaceutical composition consisting of:
   - (a) a complex formed by
     - (ai) radionuclide $^{177}$Lutetium (Lu-177), and
     - (aii) NeoB of formula (I):

(I)

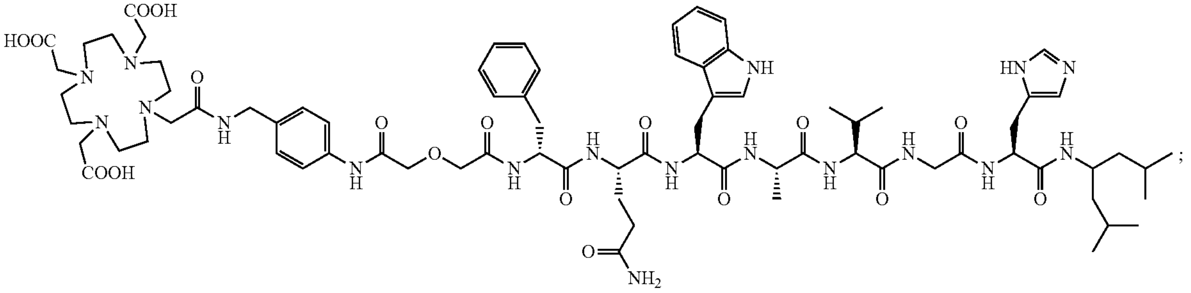

and;

(b) gentisic acid or salts thereof and ascorbic acid or salts thereof;

(c) Macrogol 15 Hydroxystearate;

(d) acetate buffer;

(e) water for injection, and (f) NaOH, (g) DTPA

25. The pharmaceutical composition according to any of the preceding embodiments wherein the pharmaceutical composition is an aqueous solution.

26. The pharmaceutical composition according to any of the preceding embodiments wherein the pharmaceutical composition is a solution for infusion.

31. The process according to embodiment 30, wherein the solution of step (1.1) comprises $^{177}LuCl_3$ as radionuclide and HCl.

32. The process according to any one of embodiments 30 to 31, wherein the solution prepared in step (1.1) comprises only one stabilizer which is gentisic acid or salt thereof in a concentration of at least 1000 μg/mL, for example between 1000 μg/mL and 1500 μg/mL.

33. The process according any one of embodiments 30 to 32, wherein the solution of step (1.1) further comprises a buffer, preferably an acetate buffer.

34. The process according to any one of embodiments 30 to 33, wherein the GRP receptor peptide antagonist binding moiety linked to a chelating agent in the solution in step (1.2) is NeoB of formula (1):

(I)

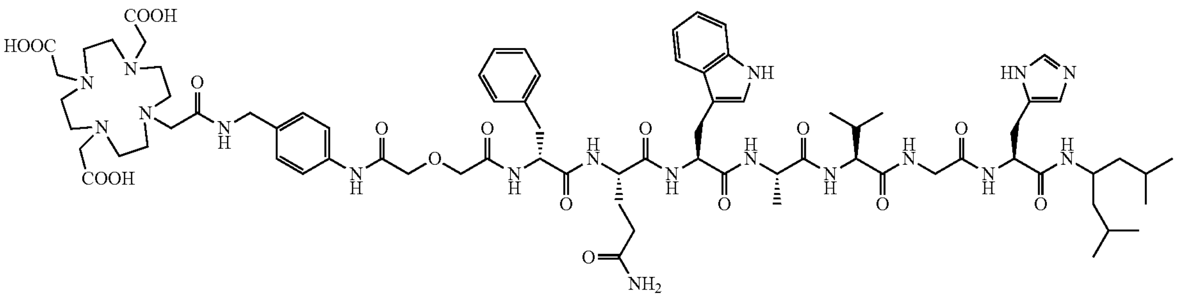

27. The pharmaceutical composition according to any of the preceding embodiments, for use in treating or preventing cancer, typically GRPR-positive cancer.

28. The pharmaceutical composition according to any one of the preceding embodiments, wherein said solution is produced at commercial scale manufacturing, in particular is produced at a batch size of at least 0.5 Ci.

29. The pharmaceutical composition according to any one of the preceding embodiments, which is for commercial use.

30. A process for manufacturing said pharmaceutical composition as defined above, comprising the process steps:

(1) Forming a complex of the radionuclide and the GRP receptor peptide antagonist binding moiety linked to a chelating agent by (1.1) preparing an aqueous solution comprising the radionuclide, and only one stabilizer which is gentisic acid or salts thereof against radiolytic degradation;

(1.2) preparing an aqueous solution comprising the GRP receptor peptide antagonist binding moiety linked to a chelating agent, and optionally a surfactant; and (1.3) mixing the solutions obtained in steps (1.1) and (1.2), heating the resulting mixture, and optionally filtering the solution obtained;

(2) Diluting the complex solution obtained by step (1) by (2.1) preparing an aqueous dilution solution optionally comprising only one stabilizer which is ascorbic acid against radiolytic degradation; and (2.2.) mixing the complex solution obtained by step (1) with the dilution solution obtained by the step (2.1) to obtain the final solution.

35. The process according any one of embodiments 30 to 34, wherein the solution of step (1.2) further comprises a surfactant which is Macrogol 15 Hydroxystearate.

36. The process according to any one of embodiments 30 to 35, wherein the solution prepared in step (2.1) comprises only one stabilizer which is ascorbic acid or salts thereof in a concentration of at least 10000 μg/mL, preferably at least 12000 μg/mL, preferably at least 15000 μg/mL, for example between 12 000 and 18 000 μg/mL.

37. The process according any one of embodiments 30 to 36, wherein the solution of step (1.2) further comprises Macrogol 15 Hydroxystearate in a concentration comprised between 5 μg/mL and 5000 μg/mL, preferably between 25 μg/mL and 2000 μg/mL, more preferably between 50 μg/mL and 1000 μg/mL, and even more preferably in a concentration of 100 μg/L.

38. The process according to any one of embodiments 30 to 37, wherein in step (1.3) the resulting mixture is heated to a temperature of from 70 to 99° C., preferably from 90 to 98° C., for from 1 to 59 min, preferably from 2 to 15 min.

39. The process according to any one of embodiments 30 to 38, wherein the complex obtained at the end of step (1.3) is further filtered through 0.20 μm.

40. The process according to any one of embodiments 30 to 39, wherein the solution of step (2.1) further comprises a sequestering agent which is diethylentriaminepentaacetic acid (DTPA) or a salt thereof.

41. The process according to any one of embodiments 30 to 40, wherein the solution of step (2.1) further comprises a pH adjuster which is NaOH.

42. The process according to any one of embodiments 30 to 41, wherein the solution of step (2.1) further comprises water for injection.

43. The process according to any one of embodiments 30 to 42, further comprising the process steps:
    (3) Sterile filtering the solution obtained by step (2):
    (4) Dispensing aseptically the filtered solution obtained by step (3) into dose unit containers wherein said radionuclide is present at a concentration that it provides a volumetric radioactivity of at least 370 MBq/mL (at EOP)+37 MBq/mL (+10%).
44. The process according to any one of embodiments 30 to 43, wherein the dose unit containers in step (4) are stoppered vials, enclosed within a lead container.
45. The pharmaceutical aqueous solution obtained by the process as defined by any one of embodiments 30 to 44.

DETAILED DESCRIPTION OF THE INVENTION

Definitions

In the following, terms as used herein are defined in their meaning.

The term "about" or "ca." has herein the meaning that the following value may vary for ±20%, preferably ±10%, more preferably ±5%, even more preferably ±2%, even more preferably ±1%.

Unless otherwise defined, "%" has herein the meaning of weight percent (wt %), also referred to as weight by weight percent (w/w %).

"total concentration": sum of one or more individual concentrations.

"aqueous solution": a solution of one or more solute in water.

"complex formed by
(ai) a radionuclide, and
(aii) a cell receptor binding organic moiety linked to a chelating agent":

The radionuclide metal ion is forming a non-covalent bond with the functional groups of the chelating agent, e.g. amines or carboxylic acids. The chelating agent has at least two such complexing functional groups to be able to form a chelate complex.

"Buffer for a pH from 4 to 6.0": may be an acetate buffer, citrate buffer (e.g. citrate+HCl or citric acid+Disodium hydrogenphosphate) or phosphate buffer (e.g. Sodium dihydrogenphosphate+Disodium hydrogenphosphate), preferably said buffer is an acetate buffer, preferably said acetate buffer is composed of acetic acid and sodium acetate.

"Sequestering agent", a chelating agent suitable to complex the radionuclide metal ions, preferably DTPA: Diethylentriaminepentaacetic acid.

"pH adjuster", is chemical that is added to a solution to adjust a pH value of the solution and to thereby achieve a desired performance. Controlling the pH can be performed by adding a pH adjuster to the formulation. Examples of pH adjusters include commonly used acids and bases, buffers and mixtures of acids and bases. For example, bases that can be used include NaOH, KOH, $Ca(OH)_2$), sodium bicarbonate, potassium carbonate, and sodium carbonate. Examples of acids that can be used include hydrochloric acid, acetic acid, citric acid, formic acid, fumaric acid, and sulfamic acid. Preferably the pH adjuster is a base, more preferably NaOH. The range of pH of the fluid can be any suitable range, such as about 2 to about 14.

"for commercial use": the drug product, e.g. a pharmaceutical aqueous solution, is able to obtain (preferably has obtained) marketing authorization by health authorities, e.g. US-FDA or EMA, by complying with all drug product quality and stability requirements as demanded by such health authorities, is able to be manufactured (preferably is manufactured) from or at a pharmaceutical production site at commercial scale followed by a quality control testing procedure, and is able to be supplied (preferably is supplied) to remotely located end users, e.g. hospitals or patients.

The chelating agent in the context of the present disclosure may be

DOTA: 1,4,7,10-Tetraazacyclododecane-1,4,7,10-tetraacetic acid,
DTPA: Diethylentriaminepentaacetic acid,
NTA: Nitrilotriacetic acid,
EDTA: Ethylenediaminetetraacetic acid,
DO3A: 1,4,7,10-Tetraazacyclododecane-1,4,7-triacetic acid,
NOTA: 1,4,7-Triazacyclononane-1,4,7-triacetic acid,
Trizoxetan,
Tetraxetan
or mixtures thereof, preferably is DOTA.

"cell receptor binding moiety": a chemical molecule which binds with at least part of its molecule to a receptor molecule at the surface of a cell. A cell receptor binding moiety, for which the present disclosure is in particular suitable, is a somatostatin receptor binding peptide, preferably said somatostatin receptor binding peptide is selected from octreotide, octreotate, lanreotide, vapreotide, pasireotide, ilatreotide, pentetreotide, depreotide, satoreotide, veldoreotide, preferably selected from octreotide and octreotate.

"linked": the cell receptor binding organic moiety is either directly linked to the chelating agent or connected via a linker molecule, preferably it is directly linked. The linking bond(s) is (are) either covalent or non-covalent bond(s) between the cell receptor binding organic moiety (and the linker) and the chelating agent, preferably the bond(s) is (are) covalent.

"Stabilizer against radiolytic degradation": stabilizing agent which protects organic molecules against radiolytic degradation, e.g. when a gamma ray emitted from the radionuclide is cleaving a bond between the atoms of an organic molecules and radicals are formed, those radicals are then scavenged by the stabilizer which avoids the radicals undergoing any other chemical reactions which might lead to undesired, potentially ineffective or even toxic molecules. Therefore, those stabilizers are also referred to as "free radical scavengers" or in short "radical scavengers". Other alternative terms for those stabilizers are "radiation stability enhancers", "radiolytic stabilizers", or simply "quenchers".

"Radiochemical purity": is that percentage of the stated radionuclide that is present in the stated chemical or biological form. Radiochromatography methods, such as HPLC method or instant Thin Layer Chromatography method (ITLC), are the most commonly accepted methods for determining radiochemical purity in the nuclear pharmacy.

As used herein, the terms "effective amount" or "therapeutically efficient amount" of a compound refer to an amount of the compound that will elicit the biological or medical response of a subject, for example, ameliorate the symptoms, alleviate conditions, slow or delay disease progression, or prevent a disease.

As used herein, the terms "substituted" or "optionally substituted" refers to a group which is optionally substituted with one or more substituents selected from: halogen, —OR', —NR'R", —SR', —SiR'R"R", —OC(O)R', —C(O)R', —$CO_2$R', —C(O)NR'R", —OC(O)NR'R", —NR"C(O)R', —NR'—C(O)NR"R", —NR"C(O)OR', —NR—C(NR'R"R")═NR"", —NR—C(NR'R")═NR"—S(O)R', —S(O) $_2$R', —S(O) $_2$NR'R", —$NRSO_2R'$, —CN, —$NO_2$, —R', —$N_3$, —$CH(Ph)_2$, fluoro ($C_1$-$C_4$)alkoxo, and fluoro ($C_1$-$C_4$)alkyl, in a number ranging from zero to the total number of open valences on aromatic ring system; and where R', R", R"' and R"" may be independently selected from hydrogen, alkyl, heteroalkyl, cycloalkyl, heterocycloalkyl, aryl and heteroaryl. When a compound of the disclosure includes more than one R group, for example, each of the R groups is independently selected as are each R', R", R"' and R"" groups when more than one of these groups is present.

As used herein, the terms "alkyl", by itself or as part of another substituent, refer to a linear or branched alkyl functional group having 1 to 12 carbon atoms. Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl).

As used herein, the terms "heteroaryl" refer to a polyunsaturated, aromatic ring system having a single ring or multiple aromatic rings fused together or linked covalently, containing 5 to 10 atoms, wherein at least one ring is aromatic and at least one ring atom is a heteroatom selected from N, O and S. The nitrogen and sulfur heteroatoms may optionally be oxidized and the nitrogen heteroatoms may optionally be quaternized. Such rings may be fused to an aryl, cycloalkyl or heterocyclyl ring. Non-limiting examples of such heteroaryl, include: furanyl, thiophenyl, pyrrolyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, indolyl, isoindolyl, benzofuranyl, isobenzofuranyl, benzothiophenyl, isobenzothiophenyl, indazolyl, benzimidazolyl, benzoxazolyl, purinyl, benzothiadiazolyl, quinolinyl, isoquinolinyl, cinnolinyl, quinazolinyl and quinoxalinyl.

As used herein, the terms "aryl" refer to a polyunsaturated, aromatic hydrocarbyl group having a single ring or multiple aromatic rings fused together, containing 6 to 10 ring atoms, wherein at least one ring is aromatic. The aromatic ring may optionally include one to two additional rings (cycloalkyl, heterocyclyl or heteroaryl as defined herein) fused thereto. Suitable aryl groups include phenyl, naphtyl and phenyl ring fused to a heterocyclyl, like benzopyranyl, benzodioxolyl, benzodioxanyl and the like.

As used herein, the term "halogen" refers to a fluoro (—F), chloro (—Cl), bromo (—Br), or iodo (—I) group.

As used herein the terms "optionally substituted aliphatic chain" refers to an optionally substituted aliphatic chain having 4 to 36 carbon atoms, preferably 12 to 24 carbon atoms. Herein after, the present disclosure is described in further detail and is exemplified.

As used herein the term "ratio between gentisic acid and ascorbic acid" is free acid concentration ratio (µg/mL:µg/mL), i.e. concentration ratio with respect to GA and AA as free acids wherein the concentration of counter-ions, such as sodium (Na), is not taken into calculation.

In general, the present disclosure is concerned about a pharmaceutical composition, in particular a radiopharmaceutical composition. The pharmaceutical composition is for intravenous (IV) use/application/administration. The solution is stable, concentrated, and ready-to-use.

The radiopharmaceutical composition according to the disclosure comprises:

(a) a complex formed by
  (ai) a radionuclide, and
  (aii) a GRP receptor peptide antagonist binding moiety linked to a chelating agent; and;
(b) at least two stabilizer against radiolytic degradation; and
(c) optionally a surfactant.

Radiolabeled GRPR-Antagonist

Said complex has the following formula:

MC—S—P wherein:

M is a radionuclide suitable for nuclear medicine,

C is a chelator which binds M,

S is an optional spacer covalently linked between C and the N-terminal of P;

P is a GRP receptor peptide antagonist, preferably of the general formula:

Xaa1-Xaa2-Xaa3-Xaa4-Xaa5-Xaa6-Xaa7-Z;

Xaa1 is not present or is selected from the group consisting of amino acid residues Asn, Thr, Phe, 3-(2-thienyl) alanine (Thi), 4-chlorophenylalanine (Cpa), α-naphthylalanine (α-Nal), β-naphthylalanine (β-Nal), 1,2,3,4-tetrahydronorharman-3-carboxylic acid (Tpi), Tyr, 3-iodo-tyrosine (o-I-Tyr), Trp and pentafluorophenylalanine (5-F-Phe) (all as L- or D-isomers);

Xaa2 is Gln, Asn or His;

Xaa3 is Trp or 1, 2, 3, 4-tetrahydronorharman-3-carboxylic acid (Tpi);

Xaa4 is Ala, Ser or Val;

Xaa5 is Val, Ser or Thr;

Xaa6 is Gly, sarcosine (Sar), D-Ala, or β-Ala;

Xaa7 is His or (3-methyl) histidine (3-Me) His;

Z is selected from —NHOH, —NHNH2, —NH-alkyl, —N(alkyl)2, and —O-alkyl or Z is

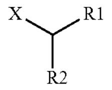

wherein X is NH (amide) or O (ester) and R1 and R2 are the same or different and selected from a proton, an optionally substituted alkyl, an optionally substituted alkyl ether, an aryl, an aryl ether or an alkyl-, halogen, hydroxyl, hydroxyalkyl, amine, amino, amido, or amide substituted aryl or heteroaryl group.

According to an embodiment, Z is selected from one of the following formulae, wherein X is NH or O:

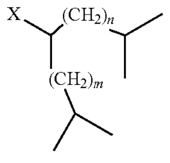

m = n = 0, 1, 2, 3

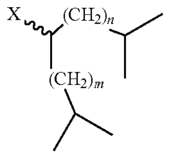

m = n = 0, 1, 2, 3

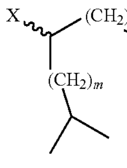

m = 0, 1, 2, 3 n = 0, 1, 2, ...9

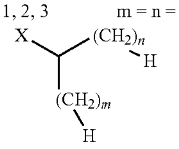

m = n = 0, 1, 2, ...9

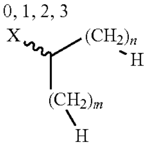

m = n = 0, 1, 2, ...9

-continued

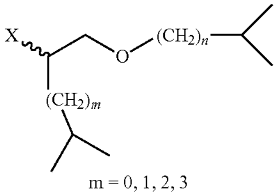

m = 0, 1, 2, 3

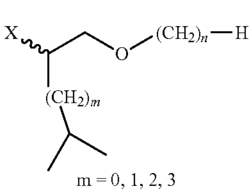

m = 0, 1, 2, 3 m = 0, 1, 2, ...5 m = 0, 1, 2, ...7

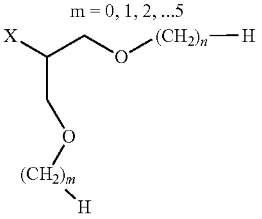

m = n = 1, 2, 3...7

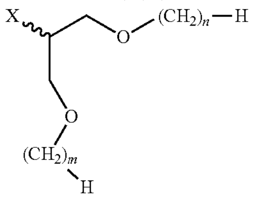

m = n = 1, 2, 3...7

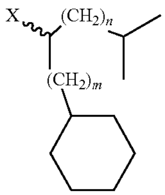

m = 0, 1, 2, 3
n = 0, 1, 2, ...7

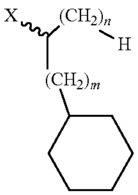

m = n = 0, 1, 2, 3
n = 0, 1, 2, ...9

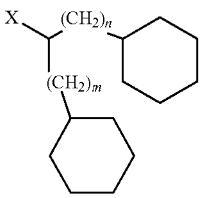

m = n = 0, 1, 2, 3

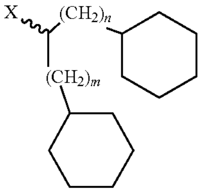

m = n = 0, 1, 2, 3
n = 0, 1, 2, ...9

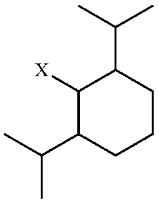

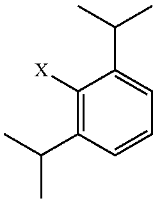

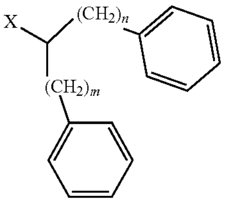

m = n = 0, 1, 2, 3

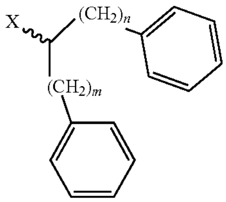

m = 0, 1, 2, 3
n = 0, 1, 2, ...9

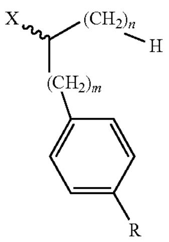

R = H, Cl, Br, I
m = 0, 1, 2, 3
n = 0, 1, 2, ...9

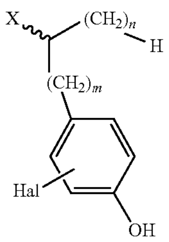

Hal = Cl, Br, I
m = 0, 1, 2, 3
n = 0, 1, 2, ...9

-continued

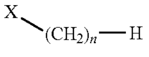

n = 1, 2, 3, ...10

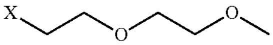

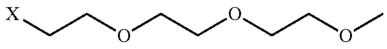

According to an embodiment, P is DPhe-Gln-Trp-Ala-Val-Gly-His-Z;

wherein Z is defined as above.

According to an embodiment, P is DPhe-Gln-Trp-Ala-Val-Gly-His-Z;

Z is selected from Leu-ψ(CH2N)-Pro-NH2 and NH—CH $(CH_2—CH(CH_3)\ _2)\ _2$ or Z is

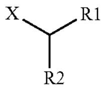

wherein X is NH (amide) and R2 is $(CH_2—CH(CH_3)\ _2$ and R1 is the same as R2 or different (CH2N)-Pro-NH2.

According to an embodiment, the chelator C is obtained by grafting one chelating agent selected among the following list:

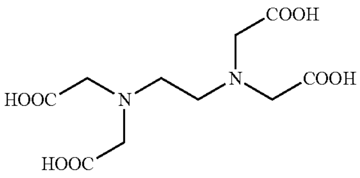

EDTA

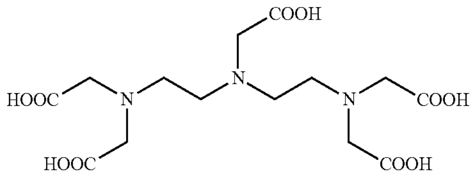

DTPA

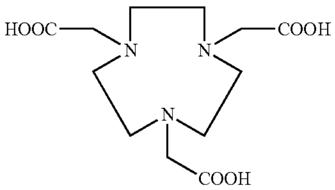

NOTA

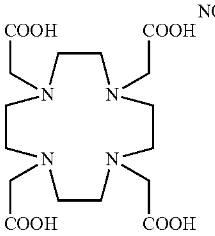

DOTA

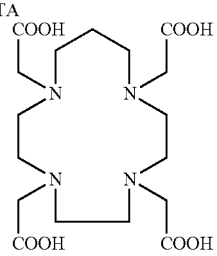

TRITA

-continued

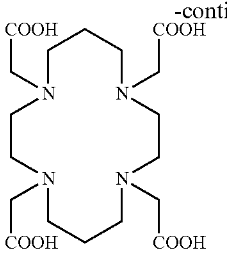

TETA

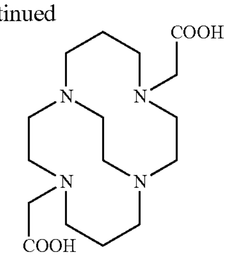

CB-TE2A

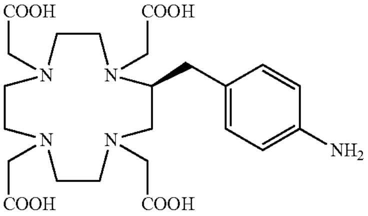

bifunctional DOTA

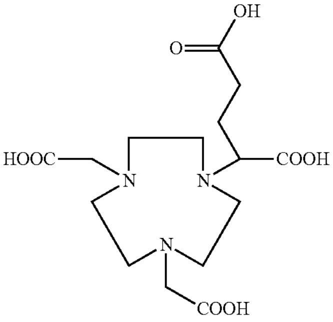

bifunctional NOTA

According to one embodiment M is a radionuclide suitable for nuclear medicine, selected from $^{111}$In, $^{18}$F, $^{211}$At, $^{82}$Rb, $^{123}$I, $^{131}$I, $^{133}$mIn, $^{99}$mTc, $^{94}$mTc, $^{67}$Ga, $^{66}$Ga, $^{68}$Ga, $^{52}$Fe, $^{169}$Er, $^{72}$As, $^{97}$Ru, $^{203}$Pb, $^{212}$Pb, $^{62}$Cu, $^{64}$Cu, $^{67}$Cu, $^{186}$Re, $^{188}$Re, $^{86}$Y, $^{90}$Y, $^{51}$Cr, $^{52}$mMn, $^{157}$Gd, $^{177}$Lu, $^{161}$Tb, $^{69}$Yb, $^{175}$Yb, $^{105}$Rh, $^{166}$Dy, $^{166}$Ho, $^{153}$Sm, $^{149}$Pm, $^{151}$Pm, $^{172}$Tm, $^{121}$Sn, $^{117}$mSn, $^{213}$Bi, $^{212}$Bi, $^{142}$Pr, $^{143}$Pr, $^{198}$Au, $^{199}$Au, $^{89}$Zr, $^{225}$Ac, $^{43}$Sc, $^{44}$Sc and $^{47}$Sc. Preferably M is selected from $^{111}$In, $^{177}$Lu, $^{225}$Ac and $^{68}$Ga According to an embodiment, the chelator C is selected from the group consisting of DOTA, DTPA, NTA, EDTA, DO3A, NOC and NOTA, preferably is DOTA.

According to an embodiment, S is selected from the group consisting of:

a) aryl containing residues of the formulae:

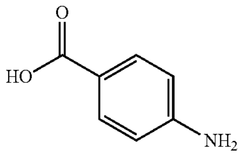

PABA

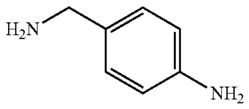

PABZA

-continued

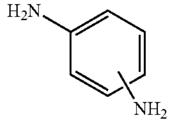

PDA

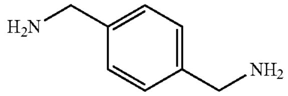

PAMBZA wherein PABA is p-aminobenzoic acid, PABZA is p-aminobenzylamine, PDA is phenylenediamine and PAMBZA is (aminomethyl)benzylamine;

b) dicarboxylic acids, ω-aminocarboxylic acids, ω-diaminocarboxylic acids or diamines of the formulae:

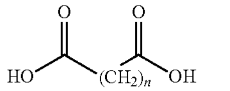

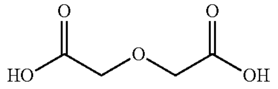

DIG

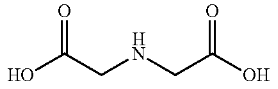

IDA

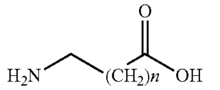

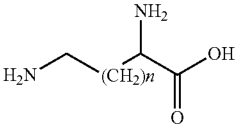

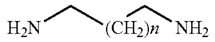

n = 0, 1, 2, . . .

wherein DIG is diglycolic acid and IDA is iminodiacetic acid;

c) PEG spacers of various chain lengths, in particular PEG spacers sele

PEG-1

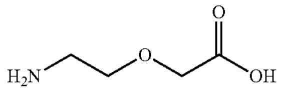

PEG-2

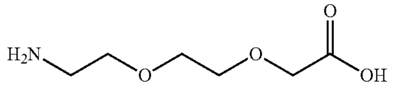

PEG-3

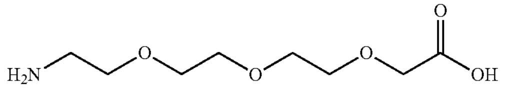

PEG-4

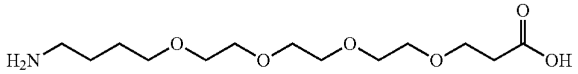

-continued

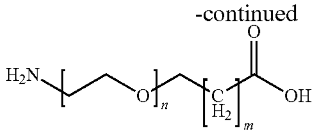

n = 1, 2, 3, . . . until 36
m = 0, 1, 2, 3, 4, 5 d) α- and β-amino acids, single or in homologous chains various chain lengths or heterologous chains of various chain lengths, in particular:

Xaa

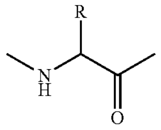

-continued

βXaa

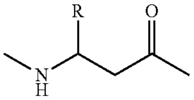

GRP (1-18), GRP (14-18), GRP (13-18), BBN (I-5), or [Tyr4] BB (1-5); or e) combinations of a, b, c and d.

According to an embodiment, the GRPR antagonist is selected from the group consisting of compounds of the following formulae:

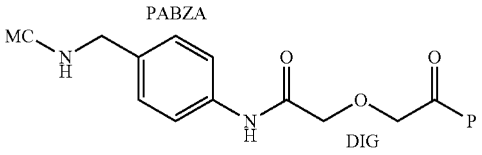

PABZA: p-Aminobenzylamine
DIG: Diglycolic acid

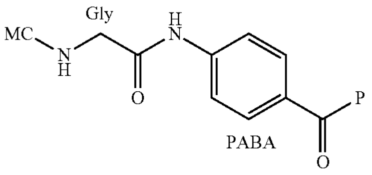

PABA: p-Aminobenzoic acid

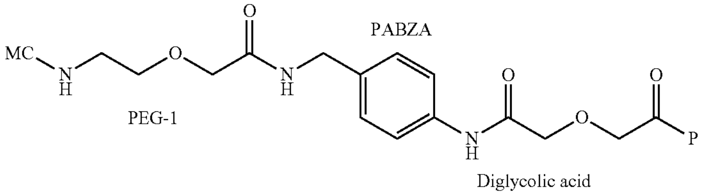

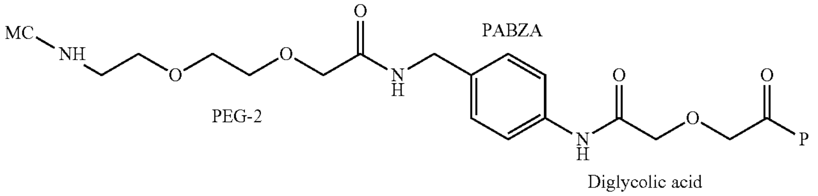

wherein MC and P are as defined above.

According to an embodiment P is DPhe-Gln-Trp-Ala-Val-Gly-His-NH—CH(CH2-CH($CH_3$) $_2$) $_2$.

According to an embodiment, said complex is NeoB1 of formula (I):

(I)

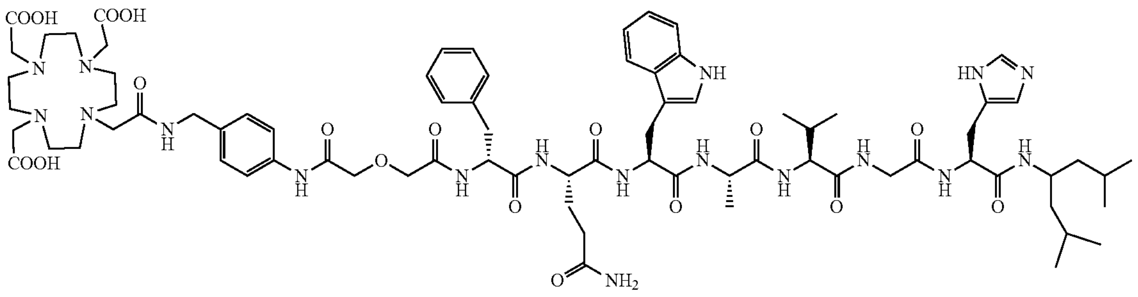

(DOTA-(p-aminobenzylamine-diglycolic acid)-[D-Phe-Gln-Trp-Ala-Val-Gly-His-NH—CH [$CH_2$—$CH(CH_3)$ $_2$]$_2$;

According to an embodiment, said complex is radiolabeled M-NeoB1 of formula (II):

(II)

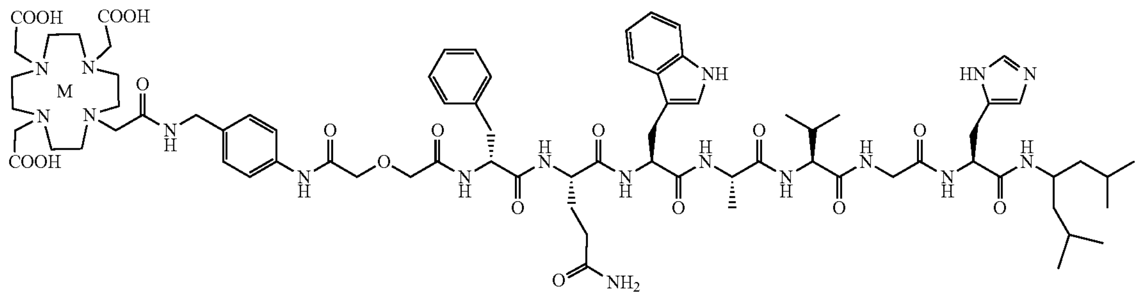

(M-DOTA-(p-aminobenzylamine-diglycolic acid)-[D-Phe-Gln-Trp-Ala-Val-Gly-His-NH—CH [$CH_2$—CH ($CH_3$) $_2$]$_2$;

wherein M is a radionuclide, preferably M is selected from $^{177}$Lu, $^{68}$Ga and $^{111}$In.

According to an embodiment, the radiolabeled GRPR-antagonist is radiolabeled NeoB2 of formula (III):

(III)

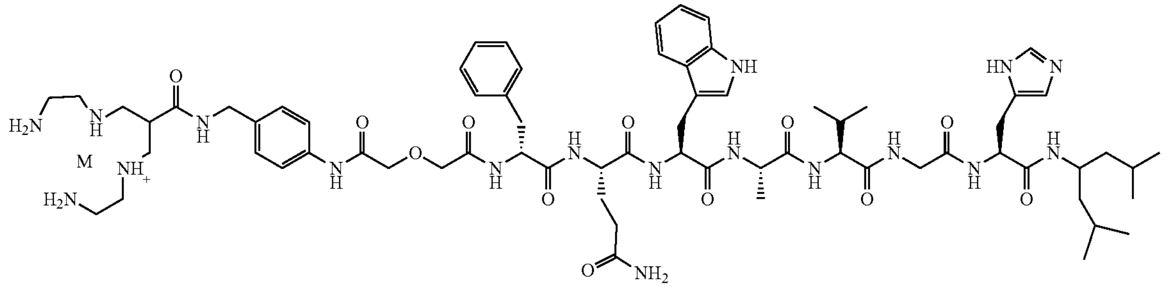

(M-$N_4$ (p-aminobenzylamine-diglycolic acid)-[D-Phe-Gln-Trp-Ala-Val-Gly-His-NH—CH [$CH_2$—$CH(CH_3)$ $_2$]$_2$;

wherein M is a radionuclide.

In an embodiment, M is a radionuclide which can be selected from selected from, $^{111}$In, $^{133}$mIn, $^{99}$mTc, $^{94}$mTc, $^{67}$Ga, $^{66}$Ga, $^{68}$Ga, $^{52}$Fe, $^{169}$Er, $^{72}$As, $^{97}$Ru, $^{203}$Pb, $^{212}$Pb, $^{62}$Cu, $^{64}$Cu, $^{67}$Cu, $^{186}$Re, $^{188}$Re, $^{86}$Y, $^{90}$Y, $^{51}$Cr, $^{52}$mMn, $^{157}$Gd, $^{177}$Lu, $^{161}$Tb, $^{69}$Yb, $^{175}$Yb, $^{105}$Rh, $^{166}$Dy, $^{166}$Ho, $^{153}$Sm, $^{149}$Pm, $^{151}$Pm, $^{172}$Tm, $^{121}$Sn, $^{117}$mSn, $^{213}$Bi, $^{212}$Bi, $^{142}$Pr, $^{143}$Pr, $^{198}$Au, $^{199}$Au, $^{89}$Zr, $^{225}$Ac and $^{47}$Sc. Preferably M is selected from $^{111}$In, $^{177}$Lu, $^{225}$Ac and $^{68}$Ga.

According to an embodiment, M is $^{177}$Lu. In this case, the radiolabeled GRPR-antagonist could be used for radionuclide therapy. According to another embodiment, M is $^{68}$Ga. In this case, the radiolabeled GRPR-antagonist could be used for PET. According to another embodiment, M is $^{111}$In. In this case, the radiolabeled GRPR-antagonist could be used for SPECT.

According to another specific embodiment, the GRPR-antagonist is ProBOMB1 of the following formula (IV):

(IV)

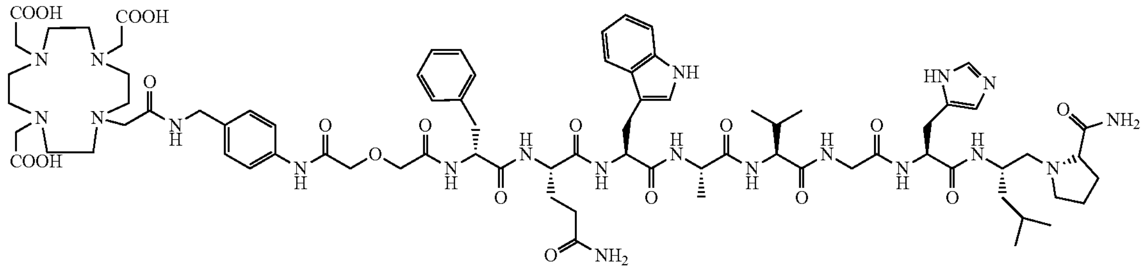

(DOTA-pABzA-DIG-D-Phe-Gln-Trp-Ala-Val-Gly-His-Leu-ψ(CH2N)-Pro-NH2)

Synthesis of the Compounds of Formula (I), (II), (III) and (IV)

The compounds of formula (I), (II), (III) and (IV) can be synthesized using the methods disclosed in the reference "*Positron Emission Tomography Imaging of the Gastrin-Releasing Peptide Receptor with a Novel Bombesin Analogue*" *ACS Omega* 2019, 4, 1470-1478.

Pharmaceutical Composition

The radiolabeled GRPR-antagonist has the tendency to degrade over time ending with radiochemical purity below the specifications at the end of the target shelf life (72 hours) which is a problem for formulating the pharmaceutical composition. The stability of the solution ascertained by the use of stabilizers against radiolytic degradation.

As used herein, "stabilizer against radiolytic degradation" refers to stabilizing agent which protects organic molecules against radiolytic degradation, e.g. when a gamma ray emitted from the radionuclide is cleaving a bond between the atoms of an organic molecules and radicals are forms, those radicals are then scavenged by the stabilizer which avoids the radicals undergo any other chemical reactions which might lead to undesired, potentially ineffective or even toxic molecules. Therefore, those stabilizers are also referred to as "free radical scavengers" or in short "radical scavengers". Other alternative terms for those stabilizers are "radiation stability enhancers", "radiolytic stabilizers", or simply "quenchers".

In general, the stabilizers used in accordance with the present inventions may be selected from gentisic acid (2,5-dihydroxybenzoic acid) or salts thereof, ascorbic acid (L-ascorbic acid, vitamin C) or salts thereof (e.g. sodium ascorbate), methionine, histidine, melatonine, ethanol, and Se-methionine. Preferred stabilizers are selected from gentisic acid or salts thereof and ascorbic acid or salts thereof.

Ethanol is considered as less preferred stabilizer due to tolerability issues associated with it if present in higher concentrations. Ethanol should be ideally avoided in the solutions of the present disclosure (in other words: free of ethanol), at least the amount of ethanol in the solutions of the present disclosure should be limited, e.g. less than 5%, preferably less than 2%, more preferably less than 1% in the final solution which is foreseen to be injected/infused. Even more preferably, the solution is free of ethanol.

In a first aspect, the present disclosure relates to a pharmaceutical composition comprising a radiolabeled GRPR-antagonist as described herein, and at least two stabilizers against radiolytic degradation.

In an embodiment, said at least two stabilizer can be selected from gentisic acid (2,5-dihydroxybenzoic acid) or salts thereof, ascorbic acid (L-ascorbic acid, vitamin C) or salts thereof (e.g. sodium ascorbate), methionine, histidine, melatonine, ethanol, and Se-methionine, preferably selected from gentisic acid or salts thereof and ascorbic acid or salts thereof. Said at least two stabilizer can be gentisic acid or salts thereof and ascorbic acid or salts thereof.

In particular, the inventors unexpectedly found that adding both ascorbic acid and gentisic acid in specific amounts in a pharmaceutical composition of a radiolabeled GRPR antagonist compound enables a radiochemical purity of said composition over 95% after 72 hours after synthesis.

In an embodiment, the ratio between gentisic acid and ascorbic acid is between 1:16 and 1:10, typically between 1:15 and 1:10, for example between 1:12 and 1:11.

In an embodiment, said gentisic acid or salts thereof can be present in a concentration of at least 1000 μg/mL, for example between 1000 μg/mL and 1500 μg/mL.

In an embodiment, said ascorbic acid or salts thereof can be present in a concentration of at least 10000 μg/mL, preferably at least 12000 μg/mL, preferably at least 15000 g/mL, for example between 12 000 and 18 000 μg/mL.

In an embodiment, said gentisic acid or salts thereof is present in a concentration of least 1000 μg/mL, for example between 1000 μg/mL and 1500 μg/mL, and ascorbic acid or salts thereof is present in a concentration of 15000 μg/mL, for example between 12 000 and 18 000 μg/mL.

In an embodiment, the radiopharmaceutical composition comprises, as radiostabilizers, both gentisic acid and ascorbic acid, at the respective concentrations of 1312 μg/mL and 15000 μg/mL.

In an embodiment, the pharmaceutical composition has radiochemical purity higher than 95% up to 72 hours, preferably higher than 98% up to 72 h.

The GRPR-antagonist has the tendency to stick to glass and plastic surfaces due to non-specific binding (NSB), which is a problem for formulating the pharmaceutical composition.

In a second aspect, the present disclosure relates to a pharmaceutical composition comprising a radiolabeled GRPR-antagonist as described herein, at least two stabilizers against radiolytic degradation and optionally a surfactant.

Said surfactant can comprise a compound having (i) a polyethylene glycol chain and (ii) a fatty acid ester. In an embodiment, the surfactant also comprises free ethylene glycol.

In an embodiment, the surfactant comprises a compound of formula (V)

(V)

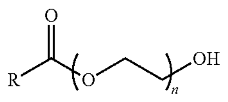

wherein n is comprised between 3 and 1000, preferably between 5 and 500, and more preferably between 10 and 50, and R is the fatty acid chain, preferably an optionally substituted aliphatic chain.

In an embodiment, the surfactant comprises polyethylene glycol 15-hydroxystearate and free ethylene glycol.

In an embodiment said surfactant is a non-ionic surfactant. Preferably said non-ionic surfactant is selected from Macrogol 15 Hydroxystearate (Kolliphor HS 15), Poloxamer (Kolliphor P188), Polysorbate 20 (Tween 20), Polysorbate 80 (Tween 80) or Polyvinylpyrrolidone average mol wt 10,000 (Polyvinylpyrrolidone K10). Preferably said non-ionic surfactant is Macrogol 15 Hydroxystearate (Kolliphor HS 15).

The radiolabeled GRPR-antagonist can be present in a concentration providing a volumetric radioactivity of at 370 MBq/mL (at EOP)+37 MBq/mL (+10%)

The surfactant can be present in a concentration of at least 5 μg/mL, preferably at least 25 μg/mL, and more preferably at least 50 μg/mL. The surfactant can be present in a concentration comprised between 5 μg/mL and 5000 μg/mL, preferably between 25 μg/mL and 2000 μg/mL, and more preferably between 50 μg/mL and 1000 μg/mL. The surfactant can be present in a concentration of 100 μg/mL.

In a third aspect, the present disclosure relates to a pharmaceutical composition comprising a radiolabeled GRPR-antagonist as described herein, at least two stabilizers against radiolytic degradation, optionally a surfactant and at least one other pharmaceutically acceptable excipient.

The pharmaceutically acceptable excipient can be any of those conventionally used, and is limited only by physico-chemical considerations, such as solubility and lack of reactivity with the active compound(s).

In particular, the one or more excipient(s) can be selected from buffer and/or solvent, and/or pH adjuster.

Buffers include acetate buffer, citrate buffer and phosphate buffer. In an embodiment said buffer is acetate buffer.

In an embodiment said solvents is water for injection.

In an embodiment said pH adjuster is NaOH.

In a fourth aspect, the present disclosure relates to a pharmaceutical composition comprising a complex formed by radionuclide 177Lutetium (Lu-177), and NeoB of formula (I):

carcinoma, gastrointestinal stromal tumors, gastrinoma, renal cell carcinomas, gastroenteropancreatic neuroendocrine tumors, oesophageal squamous cell tumors, neuroblastomas, head and neck squamous cell carcinomas, as well as ovarian, endometrial and pancreatic tumors displaying neoplasia-related vasculature that is GRPR. In an embodiment, the cancer is prostate cancer or breast cancer.

In another aspect of the invention, the pharmaceutical composition is produced at commercial scale manufacturing, in particular is produced at a batch size of at least 0.5 Ci.

In another aspect of the invention, the pharmaceutical composition is for commercial use.

In a further aspect, the disclosure also relates a pharmaceutical composition comprising a radiolabeled GRPR-antagonist, typically $^{177}$Lu-NeoB, for use in treating or preventing cancer in a subject in need thereof, wherein said pharmaceutical composition is formulated with radiostabilizers as described in any of the previous embodiments, and (I)

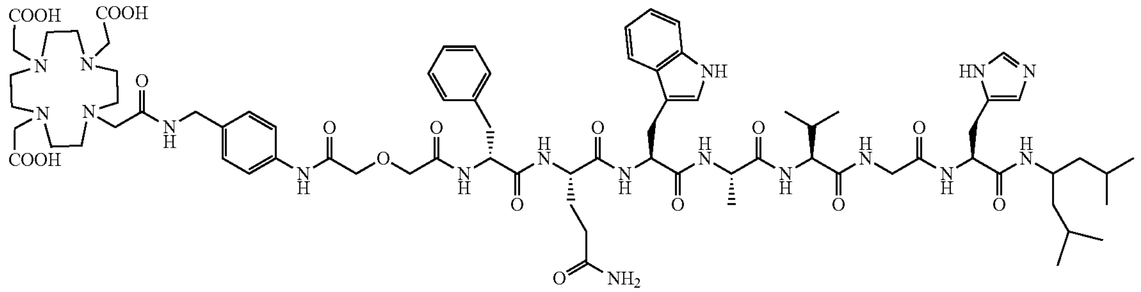

(DOTA-(p-aminobenzylamine-diglycolic acid)-[D-Phe-Gln-Trp-Ala-Val-Gly-His-NH—CH [$CH_2$—$CH(CH_3)$ $_2$]$_2$ And, gentisic acid or salts thereof and ascorbic acid or salts thereof, Macrogol 15 Hydroxystearate, acetate buffer, water for injection, and NaOH.

According to an embodiment the pharmaceutical composition is an aqueous solution, for example an injectable formulation. According to a particular embodiment, the pharmaceutical composition is a solution for infusion.

The requirements for effective pharmaceutical carriers for injectable compositions are well-known to those of ordinary skill in the art (see, e.g., Pharmaceutics and Pharmacy Practice, J.B. Lippincott Company, Philadelphia, PA, Banker and Chalmers, eds., pages 238-250 (1982), and ˆSHP Handbook on Injectable Drugs, Trissel, 15th ed., pages 622-630 (2009)).

The disclosure also relates to the pharmaceutical composition as described above for use in treating or preventing cancer, typically GRPR-positive cancer.

As used herein, the terms “cancer” refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

In specific embodiments, the cancer is selected from prostate cancer, breast cancer, small cell lung cancer, colon is administered to said subject at a therapeutically efficient amount comprised between 2000 and 10000 MBq, typically with a radiochemical purity (RCP) superior to 95% at the time of administration.

In certain aspects the subject is a mammal, for example but not limited to a rodent, canine, feline, or primate. In preferred aspects, the subject is a human.

In specific embodiments, a therapeutically efficient amount of the composition is administered to said subject 2 to 8 times per treatment.

For example, a human patient may be treated with said pharmaceutical composition comprising a radiolabeled GRPR-antagonist, specifically 177Lu-NeoB, administered intravenously in 2 to 8 cycles of a 2000 to 10000 MBq each, typically with radiochemical purity (RCP) superior to 95% at the time of administration.

In accordance with the present disclosure the following embodiments are provided:

1. A pharmaceutical composition comprising:
   (a) a complex formed by
      (ai) a radionuclide, and
      (aii) a GRP receptor peptide antagonist binding moiety linked to a chelating agent; and;
   (b) at least two stabilizer against radiolytic degradation; and
   (c) optionally a surfactant.
2. The pharmaceutical composition according to embodiment 1, wherein said radionuclide is selected from $^{111}$In, $^{18}$F, $^{211}$At, $^{82}$Rb, $^{123}$I, $^{131}$I, $^{133}$mIn, $^{99}$mTc, $^{94}$mTc, $^{67}$Ga, $^{66}$Ga, $^{68}$Ga, $^{52}$Fe, $^{169}$Er, $^{72}$As, $^{97}$Ru, $^{203}$Pb, $^{212}$Pb, $^{62}$Cu, $^{64}$Cu, $^{67}$Cu, $^{186}$Re, $^{188}$Re, $^{86}$Y, $^{90}$Y, $^{51}$Cr, $^{52}$mMn, $^{157}$Gd, $^{177}$Lu, $^{161}$Tb, $^{69}$Yb, $^{175}$Yb, $^{105}$Rh, $^{166}$Dy, $^{166}$Ho, $^{153}$Sm, $^{149}$Pm, $^{151}$Pm, $^{172}$Tm, $^{121}$Sn, $^{117}$mSn, $^{213}$Bi, $^{212}$Bi, $^{142}$Pr, $^{143}$Pr, $^{198}$Au, $^{199}$Au, $^{89}$Zr, $^{225}$Ac, $^{43}$Sc, $^{44}$Sc and $^{47}$Sc. Preferably M is selected from $^{111}$In, $^{177}$Lu, $^{225}$Ac and $^{68}$Ga, more preferably is $^{177}$Lu.

3. The pharmaceutical composition according to embodiment 1, wherein said radionuclide is present at a concentration that it provides a volumetric radioactivity of at least 370 MBq/mL (at EOP)±37 MBq/mL (±10%).
4. The pharmaceutical composition according to embodiment 1, wherein said chelating agent is selected from DOTA, DTPA, NTA, EDTA, DO3A, NOC and NOTA, preferably is DOTA.
5. The pharmaceutical composition according to embodiment 1, wherein said GRP receptor peptide antagonist binding moiety linked to a chelating agent is NeoB of formula (I):

11. The pharmaceutical composition according to embodiment 7 to 10, wherein said gentisic acid or salts thereof is present in a concentration of least 1000 μg/mL, for example between 1000 μg/mL and 1500 μg/mL, and ascorbic acid or salts thereof is present in a concentration of 15000 μg/mL, for example between 12 000 and 18 000 μg/mL.
12. The pharmaceutical composition according to embodiment 1 to 11, wherein said pharmaceutical formulation has a radiochemical purity higher than 95% up to 72 hours, preferably higher than 98% up to 72 h.
13. The pharmaceutical composition according to embodiment 1 to 12, wherein said surfactant is a non-ionic surfactant.

(I)

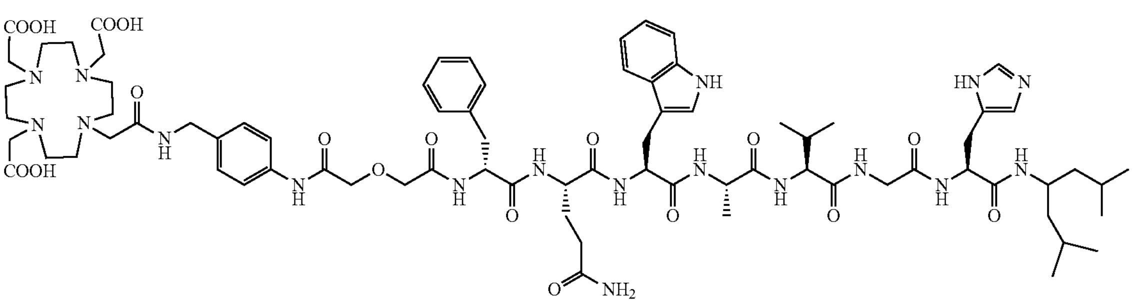

6. The pharmaceutical composition according to embodiment 1, wherein said at least two stabilizer are selected from gentisic acid (2,5-dihydroxybenzoic acid) or salts thereof, ascorbic acid (L-ascorbic acid, vitamin C) or salts thereof (e.g. sodium ascorbate), methionine, histidine, melatonine, ethanol, and Se-methionine, preferably selected from gentisic acid or salts thereof and ascorbic acid or salts thereof.
7. The pharmaceutical composition according to embodiment 6, wherein said at least two stabilizer are gentisic acid or salts thereof and ascorbic acid or salts thereof.
8. The pharmaceutical composition according to embodiment 7, wherein the ratio between gentisic acid and ascorbic acid is between 1:16 and 1:10, typically between 1:15 and 1:10, for example between 1:12 and 1:11.
9. The pharmaceutical composition according to embodiment 7 or 8, wherein said gentisic acid or salts thereof is present in a concentration of least 1000 μg/mL, for example between 1000 μg/mL and 1500 μg/mL.
10. The pharmaceutical composition according to embodiment 7 to 9, wherein said ascorbic acid or salts thereof is present in a concentration of at least 10000 μg/mL, preferably at least 12000 μg/mL, preferably at least 15000 μg/mL, for example between 12 000 and 18 000 μg/mL.
14. The pharmaceutical composition according to embodiment 13, wherein said non-ionic surfactant is selected from Macrogol 15 Hydroxystearate, Poloxamer, Polysorbate 20, Polysorbate 80 or Polyvinylpyrrolidone average mol wt 10.000.
15. The pharmaceutical composition according to embodiment 14, wherein said non-ionic surfactant is Macrogol 15 Hydroxystearate.
16. The pharmaceutical composition according to embodiment 1-15, wherein said surfactant is present in a concentration of at least 5 μg/mL, preferably at least 25 μg/mL, and more preferably at least 50 μg/mL.
17. The pharmaceutical composition according to embodiment 16, wherein said surfactant is present in a concentration comprised between 5 μg/ml and 5000 μg/mL, preferably between 25 μg/mL and 2000 μg/mL, and more preferably between 50 μg/mL and 1000 μg/mL.
18. The pharmaceutical composition according to embodiment 17, wherein said surfactant is present in a concentration of 100 g/mL.
19. A pharmaceutical composition comprising:
   (b) a complex formed by
      (ai) the radionuclide $^{177}$Lutetium (Lu-177), and
      (aii) NeoB of formula (I):

(I)

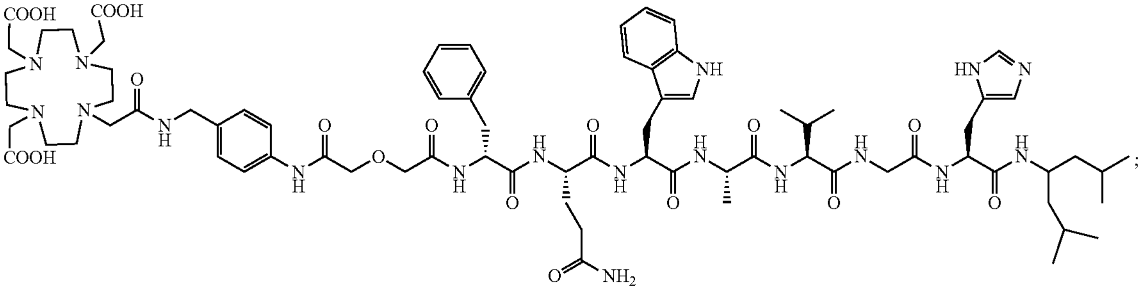

and;

(b) gentisic acid or salts thereof and ascorbic acid or salts thereof;

(c) optionally, Macrogol 15 Hydroxystearate, (d) optionally, at least one other pharmaceutically acceptable excipient.

20. The pharmaceutical composition according to embodiment 19, wherein the at least one other pharmaceutically acceptable excipient is selected from buffer and/or solvent, and/or pH adjuster.

21. The pharmaceutical composition according to embodiment 20, wherein the buffer is selected from acetate buffer, citrate buffer and phosphate buffer, preferably acetate buffer.

22. The pharmaceutical composition according to embodiment 20 or 21, wherein the solvent is water for injection.

23. The pharmaceutical composition according to embodiment 20, 21 or 22, wherein the pH adjuster is NaOH.

24. A pharmaceutical composition consisting of:

(a) a complex formed by (ai) radionuclide $^{177}$Lutetium (Lu-177), and (aii) NeoB of formula (I):

26. The pharmaceutical composition according to any of the preceding embodiments wherein the pharmaceutical composition is a solution for infusion.

27. The pharmaceutical composition according to any of the preceding embodiments, for use in treating or preventing cancer, typically GRPR-positive cancer.

28. The pharmaceutical composition according to any one of the preceding embodiments, wherein said solution is produced at commercial scale manufacturing, in particular is produced at a batch size of at least 0.5 Ci.

29. The pharmaceutical composition according to any one of the preceding embodiments, which is for commercial use.

30. A process for manufacturing said pharmaceutical composition as defined above, comprising the process steps:

(1) Forming a complex of the radionuclide and the GRP receptor peptide antagonist binding moiety linked to a chelating agent by (1.1) preparing an aqueous solution comprising the radionuclide, and only one stabilizer which is gentisic acid or salts thereof against radiolytic degradation;

(I)

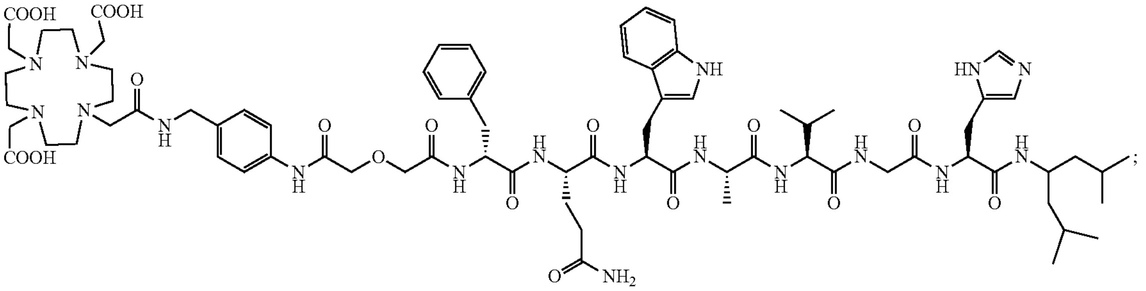

and;

(b) gentisic acid or salts thereof and ascorbic acid or salts thereof;

(c) Macrogol 15 Hydroxystearate;

(d) acetate buffer;

(e) water for injection, and (f) NaOH.

(g) DTPA

25. The pharmaceutical composition according to any of the preceding embodiments wherein the pharmaceutical composition is an aqueous solution.

(1.2) preparing an aqueous solution comprising the GRP receptor peptide antagonist binding moiety linked to a chelating agent, and optionally a surfactant; and (1.3) mixing the solutions obtained in steps (1.1) and (1.2), heating the resulting mixture, and optionally filtering the complex obtained;

(2) Diluting the complex solution obtained by step (1) by (2.1) preparing an aqueous dilution solution optionally comprising only one stabilizer which is ascorbic acid against radiolytic degradation; and (2.2.) mixing the complex solution obtained by step (1) with the dilution solution obtained by the step (2.1) to obtain the final solution.

31. The process according to embodiment 30, wherein the solution of step (1.1) comprises $^{177}LuCl_3$ as radionuclide and HCl.
32. The process according to any one of embodiments 30 to 31, wherein the solution prepared in step (1.1) comprises only one stabilizer which is gentisic acid or salt thereof in a concentration of at least 1000 μg/mL, for example between 1000 μg/mL and 1500 μg/mL.
33. The process according any one of embodiments 30 to 32, wherein the solution of step (1.1) further comprises a buffer, preferably an acetate buffer.
34. The process according to any one of embodiments 30 to 33, wherein the GRP receptor peptide antagonist binding moiety linked to a chelating agent in the solution in step (1.2) is NeoB of formula (I):

(I)

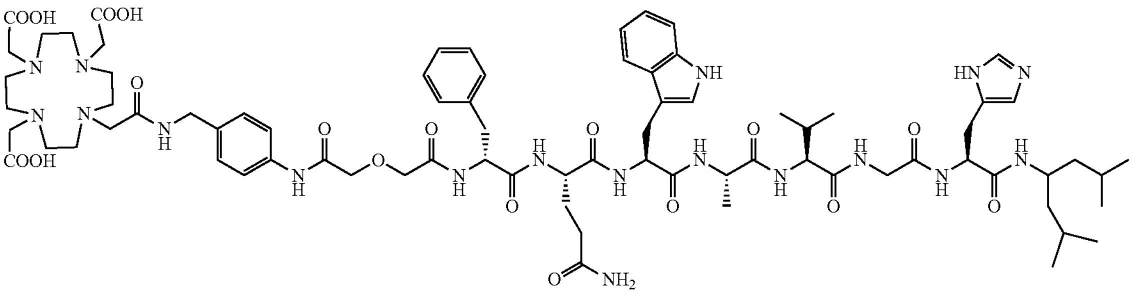

35. The process according any one of embodiments 30 to 34, wherein the solution of step (1.2) further comprises a surfactant which is Macrogol 15 Hydroxystearate.
36. The process according to any one of embodiments 30 to 35, wherein the solution prepared in step (2.1) comprises only one stabilizer which is ascorbic acid or salts thereof in a concentration of at least 10000 μg/mL, preferably at least 12000 μg/mL, preferably at least 15000 μg/mL, for example between 12 000 and 18 000 μg/mL.
37. The process according any one of embodiments 30 to 36, wherein the solution of step (1.2) further comprises Macrogol 15 Hydroxystearate in a concentration comprised between 5 μg/mL and 5000 μg/mL, preferably between 25 μg/mL and 2000 μg/mL, more preferably between 50 μg/mL and 1000 μg/mL, and even more preferably in a concentration of 100 μg/L.
38. The process according to any one of embodiments 30 to 37, wherein in step (1.3) the resulting mixture is heated to a temperature of from 70 to 99° C., preferably from 90 to 98° C., for from 1 to 59 min, preferably from 2 to 15 min.
39. The process according to any one of embodiments 30 to 38, wherein the complex obtained at the end of step (1.3) is further filtered through 0.20 μm.
40. The process according to any one of embodiments 30 to 39, wherein the solution of step (2.1) further comprises a sequestering agent which is diethylentriamine-pentaacetic acid (DTPA) or a salt thereof.
41. The process according to any one of embodiments 30 to 40, wherein the solution of step (2.1) further comprises a pH adjuster which is NaOH.
42. The process according to any one of embodiments 30 to 41, wherein the solution of step (2.1) further comprises water for injection.
43. The process according to any one of embodiments 30 to 42, further comprising the process steps:
    (3) Sterile filtering the solution obtained by step (2):
    (4) Dispensing aseptically the filtered solution obtained by step (3) into dose unit containers wherein said radionuclide is present at a concentration that it provides a volumetric radioactivity of at least 370 MBq/mL (at EOP)+37 MBq/mL (+10%).
44. The process according to any one of embodiments 30 to 43, wherein the dose unit containers in step (4) are stoppered vials, enclosed within a lead container.
45. The pharmaceutical aqueous solution obtained by the process as defined by any one of embodiments 30 to 44.

EXAMPLES

Hereinafter, the present disclosure is described in more details and specifically with reference to the examples, which however are not intended to limit the present invention.

Materials:

The $^{177}LuCl_3$ may be obtained from commercial sources, e.g. I.D.B. Holland BV. All other components of the drug product are commercially available from various sources.

Methods for Preparing the Pharmaceutical Composition

Lu-NeoB manufacturing is performed automatically by using the MiniAIO synthesizer. The synthesis procedure has been developed as follows:

1. Transferring of $^{177}LuCl_3$ into reactor;
2. Transferring of the reaction buffer into reactor. The reaction buffer is composed of sodium acetate buffer and gentisic acid. The acetate buffer allows to maintain the labelling pH between 4-5, while the gentisic acid protects the peptide from radiolysis during the labelling step;
3. Addition of the NeoB solution containing Kolliphor HS 15 into reactor;
4. Heating at 95° C. for 5 minutes;

Addition, at the end of labelling, of the dilution solution in order to obtain a volumetric activity of 10 mCi/mL. The dilution solution is composed of ascorbic acid (antioxidant agent), DTPA (sequestering agent), NaOH (pH adjuster) and water for injection.

Example 1: Effect of the Formulation on Drug Product Radiochemical Purity

The stability of the $^{177}$Lu-labelled product over 72 hours with the same antioxidant amount present in the Lutathera formulation. In particular, the following conditions are reproduced:

Gentisic acid 630 μg/mL added before the labelling step;
Kolliphor HS 15:1 mg added before the labelling step;
Peptide: Lu ratio≥1.5;
Ascorbic acid 2795 μg/mL added at the end of reaction during the formulation step;
Final volumetric Activity 10 mCi/mL;
Final pH 4-6;
Reaction buffer: Acetic acid/acetate buffer;

The radiolabelling tests are carried out both manually and automatically by using the MiniAlO synthesizer. The synthesis procedure is developed as follows:

1. Transferring of $^{177}LuCl_3$ into reactor;
2. Transferring of the reaction buffer into reactor. The reaction buffer is composed of sodium acetate buffer and gentisic acid. The acetate buffer allows to maintain the labelling pH between 4-5, while the gentisic acid protects the peptide from radiolysis during the labelling step;
3. Addition of the NeoB1 solution containing Kolliphor HS 15 into reactor;
4. Heating at 95° C. for 5 minutes;

Addition, at the end of labelling, of the dilution solution in order to obtain a volumetric activity of 10 mCi/mL. The dilution solution is composed of ascorbic acid (antioxidant agent), DTPA (sequestering agent), NaOH (pH adjuster) and water for injection.

TABLE 1

Effect of the formulation on Drug Product radiochemical purity

| Batch number | Act (mCi) | pH | RCP at t0 h (%) | RCP at t24 h (%) | RCP at t48 h (%) | RCP at the end of shelf life (%) |
|---|---|---|---|---|---|---|
| 161019A | 276.3 | 5.12 | 97.23 | 95.42 | 93.60* | ND |

*The result is out of specification

As demonstrated by the results shown in table 1, the product formulated in the same condition as Lutathera progressively degraded over time ending with a radiochemical purity below the specifications at the end of the target shelf life (72 hours).

Consequently, the development of $^{177}$LuNeoB has focused on the identification of the suitable amount of gentisic acid and ascorbic acid able to exert the desired protective function, without interfering in the labelling step.

Example 2: Identification of the Suitable Formulation to Improve Radiochemical Purity of the Drug Product Antioxidants/free radical scavengers such as ascorbic acid and gentisic acid are typically used in radiopharmaceuticals preparation to protect the labelled molecules from radiolytic degradation.

Therefore, in order to identify the suitable formulation to improve radiochemical purity, different formulations are tested by increasing the gentisic acid or ascorbic acid amount and keeping constants all the others conditions, including the amount of the other antioxidant agent.

change in the rate of gentisic acid

Firstly, we investigate the influence of the change in the rate of gentisic acid. To do that, we test the increase of the gentisic acid amount while keeping constants all the others conditions, including the amount of ascorbic acid.

As described in the table below, different concentrations of gentisic acid is tested, adding up to 1000 μg/mL in the following conditions:

Gentisic acid added before the labelling step;
Kolliphor HS 15:1 mg added before the labelling;
Ascorbic acid 2700 μg/mL added at the end of labelling during the formulation step;
Final volumetric Activity 10 mCi/mL;
Peptide: Lu ratio≥1.5;
Final pH 4-6;
Reaction buffer: Acetic acid/acetate buffer;

TABLE 2

Effect of gentisic acid on Drug Product radiochemical purity

| Batch number | Act (mCi) | Gentisic acid content (μg/mL) | Ascorbic acid content (μg/mL) | Radiochemical purity (%) at t0 h | Radiochemical purity (%) at end of shelf life |
|---|---|---|---|---|---|
| 161025A | 65 | 900 | 2700 | 98.99 | 94.78* |
| 161024A | 60 | 1000 | 2700 | 99.33 | 94.75* |

*The result is out of specification

The results as presented in table 2 demonstrate that, when the concentration of ascorbic acid is set at 2700 μg/mL and with a maximum concentration of gentisic acid of 1000 μg/mL, the radiochemical purity does not meet the specifications at the end of shelf life.

Therefore the change in the rate of gentisic acid does not influence the radiochemical purity.

change in the rate of ascorbic acid

Afterwards, we investigate the influence of different amounts of ascorbic acid on the finished product stability. As described in the table below, different concentrations of ascorbic acid have been tested, adding up to 15000 μg/mL in the following conditions:

Gentisic acid 1000 μg/mL added before the labelling step;
Kolliphor HS 15:1 mg added before the labelling;
Ascorbic acid added at the end of labelling during the formulation step;
Final volumetric Activity 10 mCi/mL;
Peptide: Lu ratio≥1.5;
Final pH 4-6;
Reaction buffer: Acetic acid/acetate buffer;

TABLE 3

Effect of ascorbic acid on Drug Product radiochemical purity at the end of synthesis and at the end of shelf life

| Batch number | Act (mCi) | Gentisic acid content (μg/mL) | Ascorbic acid content (μg/mL) | Radiochemical purity (%) at t0 h | Radiochemical purity (%) at end of shelf life |
|---|---|---|---|---|---|
| 161024A | 60.0 | 1000 | 2700 | 99.33 | 94.75* |
| 170207C | 50.0 | 1000 | 5000 | 97.34 | 93.84* |
| 170213A | 58.5 | 1000 | 10000 | 97.98 | 96.21 |
| 170628A | 120.0 | 1000 | 12000 | 97.24 | 95.17 |
| 170421A | 203 | 1000 | 15000 | 98.65 | 98.57 |

*The result is out of specifications

As demonstrated by the results shown in table 3, the radiochemical purity of drug product is higher than 95% up to 72 hours for the formulation containing at least 1000 μg/ml of gentisic acid and 10000 μg/mL of ascorbic acid. The tests carried out by increasing the ascorbic acid concentration show a clear improvement in the stability of the product at 15000 μg/mL (RCP % at end of shelf life >98%).

Evaluation of the antioxidant properties of ascorbic acid by removing the gentisic acid from the liquid formulation Based on the results shown in table 3, the minimum amount of ascorbic acid for these tests was set as 15000 μg/mL. As described in table 4, gentisic acid is not part of the formulation; there is only ascorbic acid as antioxidant. The following conditions are applied:

Kolliphor HS 15:1 mg added before the labelling;

Ascorbic acid 15000 μg/mL added at the end of labelling during the formulation step;

Final volumetric Activity 10 mCi/mL;

Peptide: Lu ratio≥1.5;

Final pH 4-6;

Reaction buffer: Acetic acid/acetate buffer;

TABLE 4

Effect of ascorbic acid on Drug Product radiochemical purity at the end of synthesis and at the end of shelf life

| Batch number | Act (mCi) | Ascorbic acid content (μg/mL) | Radiochemical purity (%) at t0 h | Radiochemical purity (%) at end of shelf life |
|---|---|---|---|---|
| 170217 | 78.0 | 15000 | 96.79 | 91.27* |

*The result is out of specification

As it can be seen, the absence of gentisic acid makes the radiochemical purity of the drug product to be below 95% after 72 hours. Therefore, based on this experimental result, gentisic acid and ascorbic acid play a complementary positive effect for the stability of the drug product.

In conclusion, the best results in terms of radiochemical stability of the product were obtained with the formulation containing both gentisic acid and ascorbic acid at a concentration respectively of 1000 μg/mL and 15000 μg/mL.

Example 3: Final Formulation Tests at 200 mCi

The study described below is designed with the aim of confirming at an activity level of 200 mCi the formulation identified through the previous development tests (examples 1-3). Based on the results described previously, the amount of gentisic and ascorbic acid are set respectively at 1000 μg/mL and at 15000 μg/mL. The synthesis is performed under the following conditions:

Gentisic acid 1000 μg/mL added from the beginning into the reactor;

Kolliphor HS 15 added into the peptide aqueous solution, final concentration 100 μg/mL;

Ascorbic acid 15000 μg/mL added at the end of labelling during the formulation step;

Final volumetric activity after formulation 10 mCi/mL;

Peptide: Lu ratio≥1.5;

Final pH 4-6;

Reaction buffer: Acetic acid/acetate buffer;

The radiolabelling is carried out automatically by using the MiniAlO synthesizer. The synthesis procedure is developed as follows:

1. Transferring of $^{177}LuCl_3$ into reactor;
2. Transferring of the reaction buffer into reactor. The reaction buffer is composed of sodium acetate buffer and gentisic acid. The acetate buffer allows to maintain the labelling pH between 4-5, while the gentisic acid protects the peptide from radiolysis during the labelling step;
3. Addition of the NeoB1 solution containing Kolliphor HS 15 into reactor;
4. Heating at 95° C. for 5 minutes;
5. Addition at the end of labelling, of the dilution solution in order to obtain 10 mCi/mL of volumetric activity. The dilution solution is composed of ascorbic acid (antioxidant agent), DTPA (sequestering agent), NaOH (pH adjuster) and saline solution.

As demonstrated by the results shown in Table 7, with 1000 μg/ml of gentisic acid and 15000 μg/mL of ascorbic acid the radiochemical purity of $^{177}$LuNeoB is always highly over 95% up to 72 hours for activities at a level of 200 mCi.

TABLE 7

Effect of the selected formulation on Drug Product radiochemical purity at the end of synthesis and at the end of shelf life

| Batch number | Act (mCi) | Gentisic acid content (μg/mL) | Ascorbic acid content (μg/mL) | Radiochemical purity (%) at t0 h | Radiochemical purity (%) at end of shelf life |
|---|---|---|---|---|---|
| 170502A | 272 | 1000 | 15000 | 98.63 | 97.60 |
| 170523A | 232 | 1000 | 15000 | 98.75 | 98.14 |
| 170929 | 187 | 1000 | 15000 | 98.58 | 98.35 |

Example 4: Final Formulation Tests at 0.5 Ci Batch

Based on the results obtained during the development of the product in R&D lab-scale, the following composition has been selected for the first scale-up batch production:

Gentisic acid 1000 μg/mL;

Ascorbic acid 15000 μg/mL;

Kolliphor HS 15 100 μg/mL;

Volumic Activity 10 mCi/mL;

Final pH 4.0-6.0;

Reaction buffer: Acetic acid/acetate buffer;

In order to move from an R&D formulation toward a Drug Product of pharmaceutical quality, the scale-up batches have been produced using the reaction buffer (product code F193,) and the formulation buffer (product code F191) produced by Gipharma and used for the production of Lutathera.

The stability of $^{177}$LuNeoB finished product has been evaluated up to 72 hours on three different sample volumes (4 mL, 6 mL and 25 mL) stored at 25±2° C.

In order to industrialize the manufacture of the Drug Substance, the scale up tests were aimed also to optimize the manufacturing process performed with the auxilium of an automatic synthesis module.

The synthesis module is used to prepare the Drug Substance (Mother Solution) containing the $^{177}$Lu-labelled molecule.

The automatic synthesis process was developed to produce the radioactive Drug Substance as a sterile, aqueous concentrate mother solution. Drug Substance synthesis steps were set up in the MiniAlO (TRASIS) synthesizer module, a self-contained closed-system synthesis module which is automated and remotely controlled by GMP compliant software with monitoring and recording of the process parameters.

Mini AlO radiosynthesizer module is widely used in the radiopharmaceutical industry for manufacture of PET radiopharmaceuticals. This module incorporate a disposable fluid path which is preferred over fixed fluid path devices since it ensures a sterile and pyrogen free fluid path and eliminates the possibility of a cross-contamination between batches.

The synthesis module is placed in a lead-shielded hot cell providing supply of Grade C HEPA filtered air. The isolator is inside a clean Grade C laboratory room.

In the Table 8 are described the target formulation characteristics selected for the manufacturing of the 0.5 Ci batch size.

TABLE 8

| Target formulation characteristics | | |
|---|---|---|
| Target Volumic activity (mCi/mL) | Target gentisic acid amount (μg/mL) | Target ascorbic acid amount (μg/mL) |
| 10 | 1000 | 15000 |

Theoretical activity of $^{177}LuCl_3$=0.5 Ci;

$^{177}LuCl_3$ specific activity at start of synthesis=9.7 Ci/mg;

NeoB1 net amount=0.600 mg;

Molar ratio (NeoB1:Lu)=1.300;

Synthesis with MiniAlO module (Trasis);

Labelling time: 5 min;

Labelling temperature: 95° C.;

In table 9 are listed some relevant IPC results obtained during the manufacturing of the $^{177}$LuNeoB1.0.5 Ci batch size.

TABLE 9

| IPC results and synthesis yield IPC results | | | |
|---|---|---|---|
| Batch number | $^{177}$Lu starting activity (mCi) | Act at the end of synthesis (mCi) | Synthesis yield (%) |
| LN171213A | 545.64 | 484.05 | 88.7% |

In order to evaluate the effects of oxidative degradation three samples volumes were dispensed at the end of production:

25 mL (VIAL-1);

4 mL (VIAL-2, VIAL-3, VIAL-4);

6 mL (VIAL-5);

In the sample VIAL-4 an extra amount of gentisic acid was added during the formulation step in order to obtain a final concentration about 1.312 mg/mL and, eventually, further decrease the radiolysis degradation.

The sample VIAL-3 has been kept under agitation for the whole stability study.

All the samples were stored at 25±2° C. The different samples dispensed are listed in table 10.

TABLE 10

| Samples characteristics and storage conditions | | | | |
|---|---|---|---|---|
| vial | Activity (mCi) | Volume (mL) | GA total amount (μg/mL) | Storage conditions |
| 1 | 250 | 25 | 1000 | RT |
| 2 | 40 | 4 | 1000 | RT |
| 3 | 40 | 4 | 1000 | RT Sample in agitation for 72 h |
| 4 | 40 | 4 | 1312 | RT |
| 5 | 60 | 6 | 1000 | RT |

Table 11 summarizes the radiochemical purity results obtained for the $^{177}$LuNeoB1 0.5 Ci scale-up batch. As it can be noted, the radiochemical purity of the product at t0 h meets the target specification being >97.00%.

The stability study performed on the VIAL-1 (25 ml sample) shows very promising results even after 72 hours, while the VIAL-2 (4 mL sample) and VIAL-3 (4 mL sample in agitation) show radiochemical purity below 95.00% at the end of the target shelf life. These preliminary results seem demonstrate the negative impact of $O_2$ on the stability of the finished product. The addition of the extra-amount of gentisic acid (sample VIAL-4) improves the stability of the finished product although the target shelf-life was not successfully met.

Finally, the VIAL-5 (6 mL sample) shows an improvement in terms of stability results compared to the 4 mL samples volumes despite the radiochemical purity at 72 h do not meet the specifications.

TABLE 11

| Quality control results | | |
|---|---|---|
| QC vial | RCP at t0 h (%) | RCP at t72 h (%) |
| 1 | 97.06 | 95.94 |
| 2 | | 91.93* |
| 3 | | 91.75* |
| 4 | | 92.78* |
| 5 | | 93.26* |

*The result is out of specification

Final Target Formulation and Detailed Composition

The final amount of ascorbic acid and gentisic acid has been defined on the basis of the data collected during the development activities. In particular, the gentisic acid at a concentration of 1312 ppm together with the ascorbic acid at a concentration of 15000 ppm has shown excellent antioxidant properties allowing for the achievement of the target shelf life.

Based on all development tests performed, the formulation selected for $^{177}$LuNeoB manufacturing at a radioactivity level up to 500 mCi is the following:

TABLE 12

| $^{177}$LuNeoB formulation | | |
|---|---|---|
| Component | Purpose | Amount for 500 mCi synthesis |
| $^{177}LuCl_3$ acqueous solution | Radioactive substance | 500 mCi (1.5 mL) |
| NeoB | Active substance | 600 μg |

TABLE 12-continued

| $^{177}$LuNeoB formulation | | |
|---|---|---|
| Component | Purpose | Amount for 500 mCi synthesis |
| Kolliphor HS 15 | Tensioactive agent | 100 μg/mL |
| Gentisic acid | Antioxidant agent | 1312 μg/mL |
| Ascorbic acid | Antioxidant agent | 15000 μg/mL |
| Acetate buffer | Buffer | Qs |
| DTPA | Sequestering agent | 370 μg/mL |
| Water for injection | Solvent | Qs |
| NaOH | pH adjuster | 4.77 mg/mL |

The invention claimed is:

1. A pharmaceutical composition comprising:
(a) a complex formed by
(ai) a radionuclide $^{177}$Lu, and
(aii) a compound of formula I (I)

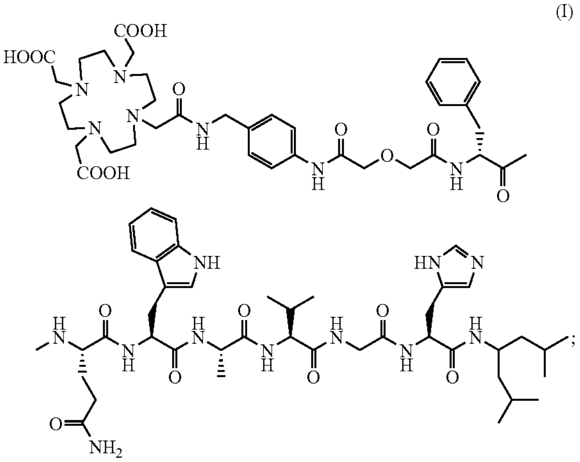

and;
(b) at least two stabilizers against radiolytic degradation which are gentisic acid or salts thereof and ascorbic acid or salts thereof,
wherein the concentration ratio in μg/mL between gentisic acid or salts thereof and ascorbic acid or salts thereof is between 1:16 and 1:10; and
(c) optionally a surfactant.

2. The pharmaceutical composition according to claim 1, wherein said radionuclide is present at a concentration providing a volumetric radioactivity of at least 370 MBq/mL at End Of Processing±37 MBq/mL.

3. The pharmaceutical composition according to claim 1, wherein said gentisic acid or salts thereof is present in a concentration of least 1000 μg/mL.

4. The pharmaceutical composition according to claim 1, wherein said ascorbic acid or salts thereof is present in a concentration of at least 10000 μg/mL.

5. The pharmaceutical composition according to claim 1, wherein said pharmaceutical formulation has a radiochemical purity higher than 95% up to 72 hours.

6. The pharmaceutical composition of claim 1 further comprising macrogol 15 hydroxystearate as a surfactant.

7. The pharmaceutical composition according to claim 6, further comprising at least one other pharmaceutically acceptable excipient selected from buffer and/or solvent, and/or pH adjuster.

8. A pharmaceutical composition consisting of:
(a) a complex formed by
(ai) radionuclide $^{177}$Lutetium (Lu-177), and
(aii) NeoB of formula (I):

(I)

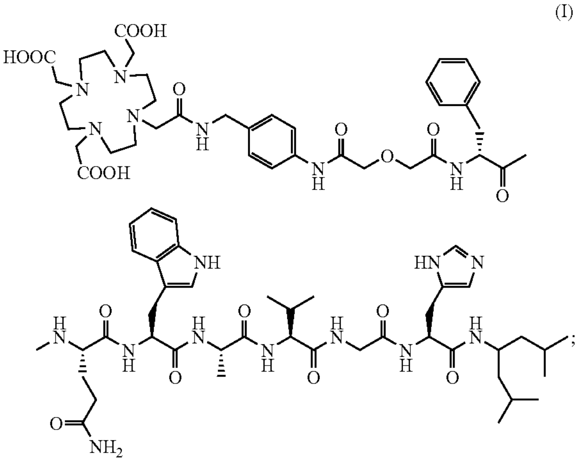

and;
(b) gentisic acid or salts thereof and ascorbic acid or salts thereof;
(c) Macrogol 15 Hydroxystearate;
(d) acetate buffer;
(e) water for injection;
(f) NaOH; and
(g) DTPA,
wherein the concentration ratio in μg/mL between gentisic acid or salts thereof and ascorbic acid or salts thereof is between 1:16 and 1:10.

* * * * *